(12) United States Patent
Aubert et al.

(10) Patent No.: US 10,130,829 B2
(45) Date of Patent: *Nov. 20, 2018

(54) PACKAGING ARTICLE COMPRISING AN ENVELOPE AND AN ANHYDROUS DYE COMPOSITION COMPRISING A DIRECT DYE, USE OF THE SAME AND PROCESS FOR DYEING KERATIN FIBRES

(71) Applicant: L'OREAL, Paris (FR)

(72) Inventors: Fabien Aubert, Paris (FR); Frédéric Guerin, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/107,258

(22) PCT Filed: Dec. 19, 2014

(86) PCT No.: PCT/EP2014/078848
§ 371 (c)(1),
(2) Date: Jun. 22, 2016

(87) PCT Pub. No.: WO2015/097098
PCT Pub. Date: Jul. 2, 2015

(65) Prior Publication Data
US 2017/0001045 A1    Jan. 5, 2017

(30) Foreign Application Priority Data
Dec. 23, 2013   (FR) ...................................... 13 63395

(51) Int. Cl.
*A61Q 5/06*    (2006.01)
*A61K 8/81*    (2006.01)
(Continued)

(52) U.S. Cl.
CPC .............. *A61Q 5/065* (2013.01); *A61K 8/022* (2013.01); *A61K 8/0208* (2013.01); *A61K 8/418* (2013.01);
(Continued)

(58) Field of Classification Search
CPC .... A61Q 5/065; A61K 8/8129; A61K 8/0208; A61K 8/022; A61K 8/418; A61K 8/8152;
(Continued)

(56) References Cited

U.S. PATENT DOCUMENTS 3,100,739 A   8/1963 Kaiser et al.
3,376,110 A   4/1968 Shiraeff
(Continued)

FOREIGN PATENT DOCUMENTS

DE   2359399 A1   6/1975
DE   2527638 A1   5/1976
(Continued)

OTHER PUBLICATIONS

International Search Report for PCT/EP2014/078851, dated Mar. 25, 2015.
(Continued)

*Primary Examiner* — Eisa B Elhilo
(74) *Attorney, Agent, or Firm* — The Marbury Law Group, PLLC

(57) ABSTRACT

The present invention relates to a packaging article comprising: i) an envelope defining at least one cavity, the envelope comprising water-soluble and/or liposoluble fibres; ii) at least one anhydrous dye composition containing at least one direct dye; and iii) optionally at least one anhydrous oxidizing agent; it being understood that the dye composition ii) and the anhydrous oxidizing agent iii), when it is present, are in one of the cavities defined by the envelope i). Another subject of the invention is the use of the
(Continued)

said article for dyeing keratin fibres and a process for dyeing keratin fibres using the said article. The use of the packaging article makes it possible to obtain dye compositions whose consistency is pleasant on use, which are easy to apply and which make it possible to obtain powerful colouring of the hair.

19 Claims, 2 Drawing Sheets

(51) Int. Cl.
    *A61K 8/02*          (2006.01)
    *A61K 8/41*          (2006.01)
    *B65D 65/46*        (2006.01)
    *A45D 19/00*        (2006.01)

(52) U.S. Cl.
    CPC .......... *A61K 8/8129* (2013.01); *A61K 8/8152* (2013.01); *B65D 65/46* (2013.01); *A45D 2019/0066* (2013.01); *A45D 2200/1036* (2013.01); *A45D 2200/1045* (2013.01); *A61K 2800/31* (2013.01); *A61K 2800/4322* (2013.01); *A61K 2800/87* (2013.01)

(58) Field of Classification Search
    CPC .......... A61K 2800/87; A61K 2800/045; A61K 2800/4322; A61K 2800/31; B65D 65/46; A45D 2019/0066; A45D 2200/1036
    See application file for complete search history.

(56) References Cited

U.S. PATENT DOCUMENTS

| | | | |
|---|---|---|---|
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,665,036 A | 5/1972 | Kalopissis et al. |
| 3,817,698 A | 6/1974 | Kalopissis et al. |
| 3,867,456 A | 2/1975 | Kalopissis et al. |
| 3,869,454 A | 3/1975 | Lang et al. |
| 3,955,918 A | 5/1976 | Lang |
| 3,985,499 A | 10/1976 | Lang et al. |
| 4,003,699 A | 1/1977 | Rose et al. |
| 4,017,460 A | 4/1977 | Tessler |
| 4,025,301 A | 5/1977 | Lang |
| 4,031,307 A | 6/1977 | DeMartino et al. |
| 4,151,162 A | 4/1979 | Lang et al. |
| 4,153,065 A | 5/1979 | Lang |
| 4,157,388 A | 6/1979 | Christiansen |
| RE30,199 E | 1/1980 | Rose et al. |
| 4,217,914 A | 8/1980 | Jacquet et al. |
| 4,226,784 A | 10/1980 | Kalopissis et al. |
| 4,348,202 A | 9/1982 | Grollier et al. |
| 4,390,689 A | 6/1983 | Jacquet et al. |
| 4,422,853 A | 12/1983 | Jacquet et al. |
| 4,579,732 A | 4/1986 | Grollier et al. |
| 4,702,906 A | 10/1987 | Jacquet et al. |
| 4,719,282 A | 1/1988 | Nadolsky et al. |
| 4,777,040 A | 10/1988 | Grollier et al. |
| 4,886,517 A | 12/1989 | Bugaut et al. |
| 4,948,579 A | 8/1990 | Jacquet et al. |
| 4,970,066 A | 11/1990 | Grollier et al. |
| 5,008,093 A | 4/1991 | Merianos |
| 5,008,106 A | 4/1991 | Merianos et al. |
| 5,061,289 A | 10/1991 | Clausen et al. |
| 5,077,047 A | 12/1991 | Biss et al. |
| 5,183,901 A | 2/1993 | Login et al. |
| 5,196,189 A | 3/1993 | Jacquet et al. |
| 5,380,340 A | 1/1995 | Neunhoeffer et al. |
| 5,455,340 A | 10/1995 | Bernard et al. |
| 5,534,267 A | 7/1996 | Neunhoeffer et al. |
| 5,663,366 A | 9/1997 | Neunhoeffer et al. |
| 5,674,436 A | 10/1997 | Breitenbach et al. |
| 5,708,151 A | 1/1998 | Mockli |
| 5,753,770 A | 5/1998 | Breitenbach et al. |
| 5,766,576 A | 6/1998 | Lowe et al. |
| 5,780,418 A | 7/1998 | Niinaka et al. |
| 5,879,413 A | 3/1999 | Pengilly et al. |
| 5,888,252 A | 3/1999 | Mockli |
| 5,919,273 A | 7/1999 | Rondeau et al. |
| 5,944,360 A | 8/1999 | Crapart |
| 5,945,032 A | 8/1999 | Breitenbach et al. |
| 5,993,490 A | 11/1999 | Rondeau et al. |
| 6,045,591 A | 4/2000 | Deneulenaere |
| 6,099,592 A | 8/2000 | Vidal et al. |
| 6,120,698 A | 9/2000 | Rounds et al. |
| 6,136,042 A | 10/2000 | Maubru |
| 6,179,881 B1 | 1/2001 | Henrion et al. |
| 6,284,003 B1 | 9/2001 | Rose et al. |
| 6,312,677 B1 | 11/2001 | Millequant et al. |
| 6,338,741 B1 | 1/2002 | Vidal et al. |
| 6,458,167 B1 | 10/2002 | Genet et al. |
| 6,492,502 B2 | 12/2002 | Henrion et al. |
| 6,645,258 B2 | 11/2003 | Vidal et al. |
| 6,730,789 B1 | 5/2004 | Birault et al. |
| 6,797,013 B1 | 9/2004 | Lang et al. |
| 6,863,883 B1 | 3/2005 | Tsujino et al. |
| 7,799,095 B2 | 9/2010 | Mario et al. |
| 9,114,088 B2 | 8/2015 | Konno et al. |
| 2001/0001332 A1 | 5/2001 | Henrion et al. |
| 2002/0050013 A1 | 5/2002 | Vidal et al. |
| 2002/0165368 A1 | 11/2002 | Henrion et al. |
| 2003/0019051 A9 | 1/2003 | Vidal et al. |
| 2004/0152610 A1 | 8/2004 | Engel et al. |
| 2006/0002965 A1* | 1/2006 | Hoeffkes .................. A61Q 5/10 424/401 |
| 2007/0134481 A1* | 6/2007 | Aubrun-Sonneville ..................... A61K 8/0208 428/292.1 |
| 2008/0263786 A1 | 10/2008 | Schmenger et al. |
| 2009/0056039 A1 | 3/2009 | Schmenger et al. |
| 2009/0151087 A1 | 6/2009 | Mario et al. |
| 2010/0064449 A1 | 3/2010 | Khan et al. |
| 2011/0033509 A1 | 2/2011 | Simon |
| 2011/0203604 A1 | 8/2011 | Hasegawa et al. |
| 2012/0207689 A1 | 8/2012 | Konno et al. |

FOREIGN PATENT DOCUMENTS

| | | |
|---|---|---|
| DE | 2538363 A1 | 5/1976 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 4344131 A1 | 6/1995 |
| DE | 19543988 A1 | 5/1997 |
| DE | 19545380 A1 | 6/1997 |
| DE | 19613941 A1 | 10/1997 |
| EP | 0557203 A1 | 8/1993 |
| EP | 0636716 A1 | 2/1995 |
| EP | 0714919 A2 | 6/1996 |
| EP | 0714954 A2 | 6/1996 |
| EP | 0770375 A1 | 5/1997 |
| EP | 0832846 A2 | 4/1998 |
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |
| EP | 1133967 A1 | 9/2001 |
| EP | 1133975 A2 | 9/2001 |
| EP | 2011474 A1 | 1/2009 |
| FR | 1221122 A | 5/1960 |
| FR | 1516943 A | 2/1968 |
| FR | 1540423 A | 8/1968 |
| FR | 1560664 A | 3/1969 |
| FR | 1567219 A | 5/1969 |
| FR | 2189006 A1 | 1/1974 |
| FR | 2270846 A1 | 12/1975 |
| FR | 2275462 A1 | 1/1976 |

(56) References Cited

FOREIGN PATENT DOCUMENTS

| | | | |
|---|---|---|---|
| FR | 2285851 A1 | 4/1976 |
| FR | 2459044 A | 1/1981 |
| FR | 2570946 A1 | 4/1986 |
| FR | 2733749 A1 | 11/1996 |
| FR | 2757385 A1 | 6/1998 |
| FR | 2788433 A1 | 7/2000 |
| FR | 2801308 A1 | 5/2001 |
| FR | 2998146 A1 | 5/2014 |
| GB | 195386 A | 2/1924 |
| GB | 738585 A | 10/1955 |
| GB | 1026978 A | 4/1966 |
| GB | 1153196 A | 5/1969 |
| GB | 1163385 A | 9/1969 |
| GB | 1514466 A | 6/1978 |
| JP | 02-019576 A | 1/1990 |
| JP | 05-163124 A | 6/1993 |
| WO | 94/08910 A1 | 4/1994 |
| WO | 94/08969 A1 | 4/1994 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 99/48465 A1 | 9/1999 |
| WO | 2011/059027 A1 | 5/2001 |
| WO | 01/66646 A1 | 9/2001 |
| WO | 03/029359 A1 | 4/2003 |
| WO | 03/044152 A1 | 5/2003 |
| WO | 2012/015034 A1 | 2/2012 |
| WO | 2015/097099 A1 | 7/2015 |
| WO | 2015/097101 A1 | 7/2015 |

OTHER PUBLICATIONS

International Search Report for PCT/EP2014/078848, dated Mar. 25, 2015.
International Search Report for PCT/EP2014/078855, dated Mar. 27, 2015.
Porter, M.R., "Handbook of Surfactants," published by Blackie & Son (Glasgow and London), 1991, pp. 116-178.
"Textile Auxiliaries," Ullmann's Encyclopedia of Industrial Chemistry, 2002, Wiley-VCH Verlag GmbH & Co. KGaA, Weinheim, 10.1002/14356007.a26 227, pp. 1-129.
"Azo Dyes," Ullmann's Encyclopedia of Industrial Chemistry, 2005, Wiley-VCH Verlag GmbH & Co., KGaA, Weinheim 10.1002/14356007.a03 245, point 3.2, pp. 1-93.
Ashford's Dictionary of Industrial Chemicals, Second Edition, 2001, pp. 14-39.
English language abstract for DE 4137005A1 (dated May 13, 1993).
English language abstract for DE 4220388A1 (dated Dec. 23, 1993).
English language abstract for DE 19545380A1 (dated Jun. 12, 1997).
English language abstract for EP 0770375A1 (dated May 2, 1997).
English language abstract for FR 2459044A (dated Jan. 9, 1981).
English language abstract for JP 02-019576A (dated Jan. 23, 1990).
English language abstract for JP 05-163124A (dated Jun. 29, 1993).
Non-Final Office Action for copending U.S. Appl. No. 15/107,289, dated Apr. 27, 2017.
Final Office Action for copending U.S. Appl. No. 15/107,289, dated Nov. 13, 2017.
Non-Final Office Action for copending U.S. Appl. No. 15/107,319, dated Apr. 16, 2018.

* cited by examiner

PACKAGING ARTICLE COMPRISING AN ENVELOPE AND AN ANHYDROUS DYE COMPOSITION COMPRISING A DIRECT DYE, USE OF THE SAME AND PROCESS FOR DYEING KERATIN FIBRES

CROSS REFERENCE TO RELATED APPLICATIONS

This is a national stage application of PCT/EP2014/078848, filed internationally on Dec. 19, 2014, which claims priority to French Application No. 1363395, filed on Dec. 23, 2013, both of which are incorporated by reference herein by their entireties.

TECHNICAL FIELD

The present invention relates to a packaging article comprising a direct dye for dyeing keratin fibres, in particular human hair.

BACKGROUND

Many people have sought for a long time to modify the colour of their hair and in particular to mask their grey hair.

It is known practice to obtain "permanent" or oxidation dyeing with dye compositions containing oxidation dye precursors, which are generally known as oxidation bases, such as ortho- or para-phenylenediamines, ortho- or para-aminophenols and heterocyclic compounds. These oxidation bases are initially colourless or weakly coloured compounds, which, when combined with oxidizing products, may give rise to coloured compounds via a process of oxidative condensation.

The variety of molecules used as oxidation bases and couplers allows a wide range of colours to be obtained.

It is also known practice to dye keratin fibres temporarily with direct dyes, which are coloured and colouring molecules that have affinity for the fibres. The direct dyes generally used are chosen from nitrobenzene, anthraquinone, nitropyridine, azo, methine, azomethine, xanthene, acridine, azine and triarylmethane direct dyes. The presence of such compounds enables the colouring obtained to be further enriched with tints or enables the chromaticity of the colouring obtained to be increased. This direct dyeing may be performed at acidic, neutral or alkaline pH and in the presence or absence of an oxidizing agent.

Dyeing, whether direct dyeing or oxidation dyeing, must moreover satisfy a certain number of requirements. Thus, it must be free of toxicological drawbacks, it must enable the desired shades to be obtained and it must show good resistance to external attacking factors such as light, bad weather, washing, permanent waving, perspiration and rubbing.

The dyeing process must also make it possible to obtain shades that are as unselective as possible, i.e. it must produce the smallest possible colour differences all along the same keratin fibre, which generally comprises areas that are differently sensitized (i.e. damaged) from its end to its root.

The compositions used in the dyeing process must also have good mixing and application properties on keratin fibres, and in particular good rheological properties so as not to run, when they are applied, onto the face, onto the scalp or beyond the areas that it is proposed to dye.

Direct dyeing is usually performed in a lightening dyeing process using at least one dye composition comprising a direct dye and at least one oxidizing composition, which are mixed together at the time of use just before application to the fibres. Specifically, it is not possible to store in the same composition all the ingredients except the water, so as to avoid degradation of the hydrogen peroxide in alkaline or neutral aqueous medium, and denaturation of the direct dyes by prolonged contact in oxidizing medium and consequently a reduction of the dyeing power of the said dyes on the keratin fibres.

Thus, according to the usual practice, the dye composition(s), on the one hand, and the oxidizing aqueous composition, on the other hand, which has an acidic pH to ensure the stability of the hydrogen peroxide, are stored separately, and are not placed in contact until the time of use.

The need to use several compositions first entails drawbacks inherent in the storage of several compositions, with a larger storage area.

This moreover entails the need to measure out the compositions before placing them in contact. To overcome this drawback, it may be proposed to use kits (or multi-compartment devices), but this nevertheless complicates the use of the compositions and increases the costs. Furthermore, in certain cases, the dye compositions and oxidizing compositions are in different galenical forms, for instance powders, granules, pastes or creams, which may complicate the mixing and the production of a homogeneous final composition (see, for example, US 2007/0006, US 2008/0 263 786, US 2009/0 056 039, US 2010/064 449, EP 23601604, WO 2012/015 034, WO 11/059 027, US 2011/203 604, FR 0 756 173 and EP 2 011 474). In addition, it is seen that the compositions derived from these powders, granules, pastes and creams do not always give compositions with textures that are easy to apply. Furthermore, the mixtures obtained do not always give the keratin fibres satisfactory colours, especially in terms of intensity, dyeing power, chromaticity and/or sparingly selective colourings, i.e. colourings that are sparingly homogeneous between the root and the end of the fibre. Moreover, they do not always lead to easy application with a suitable consistency.

Furthermore, during the use of pulverulent dye compositions, there may be a risk of the user coming into contact with the dyes and the alkaline agents.

SUMMARY

One aim of the present invention is thus to propose a composition to be used in a direct dyeing process, which makes it possible simultaneously to solve the problem of the storage area, the stability of the storage, which avoids any direct contact of the dyes and other ingredients used in the direct dyeing, such as the alkaline agents and the chemical oxidizing agents, with the user, and which is easy to use by mixing with an oxidizing composition prior to its use, or simply with an aqueous solution such as water, or with a liquid fatty substance such as liquid petroleum jelly. The mixture is pleasant to manipulate and has a composition rheology that prevents the dye composition from running outside the areas that it is desired to dye. An aim of the present invention is also for the colours obtained on keratin fibres treated with the packaging article to be sparingly selective, intense, powerful, chromatic and persistent, especially with respect to shampooing and to light.

This/these aim(s) is/are achieved by the present invention, one subject of which is a packaging article comprising:
i) an envelope defining at least one cavity, the envelope comprising water-soluble and/or liposoluble fibres, preferably water-soluble polymer fibres;

ii) at least one anhydrous dye composition, preferably in paste or powder form, containing at least one direct dye; and iii) optionally at least one anhydrous oxidizing agent, preferably in paste or powder form, it being understood that the dye composition ii) and the oxidizing agent iii), when it is present, are in one of the cavities defined by the envelope i).

Another object of the invention is a process for treating keratin fibres, especially human keratin fibres such as the hair, comprising at least a step of carrying out a packaging article as defined herein before. More particularly a process for dyeing keratin fibres, especially human keratin fibres such as the hair, comprising the following steps: i) mixing the packaging article of the invention with a composition that is capable of dissolving the packaging article, ii) applying the resulting composition to the keratin fibres, iii) leaving the composition to stand on the fibres, iv) rinsing the said fibres, v) optionally shampooing the fibres, rinsing them and drying them, the composition that is capable of dissolving the packaging article possibly containing an oxidizing agent.

Another subject of the invention is the use of the packaging article as defined previously for dyeing keratin fibres, preferably the hair.

The use of the packaging article makes it possible to obtain keratin fibre dye compositions whose consistency is pleasant on use, which are easy to apply and which do not run outside the areas to be treated. The colourings obtained on the keratin fibres have excellent dyeing properties especially in terms of the chromaticity, selectivity, intensity or persistence, which are identical, comparable to or even better than those of compositions with standard packaging, i.e. in separate liquid form. In addition, the packaging article of the invention makes it possible for there no longer to be direct contact between the user and the powdered ingredients.

Moreover, the packaging article has a size that is reduced to its strict minimum, very compact, without bulky packaging.

Other characteristics and advantages of the invention will emerge more clearly on reading the description and the examples that follow.

BRIEF DESCRIPTION OF THE DRAWINGS

The accompanying drawings, which are included to provide a further understanding of the invention and are incorporated in and constitute a part of this specification, together with the description, serve to explain the principles of the invention.

FIG. 1b is a top view of the packaging article of FIG. 1a,

DETAILED DESCRIPTION

Figure 1A:
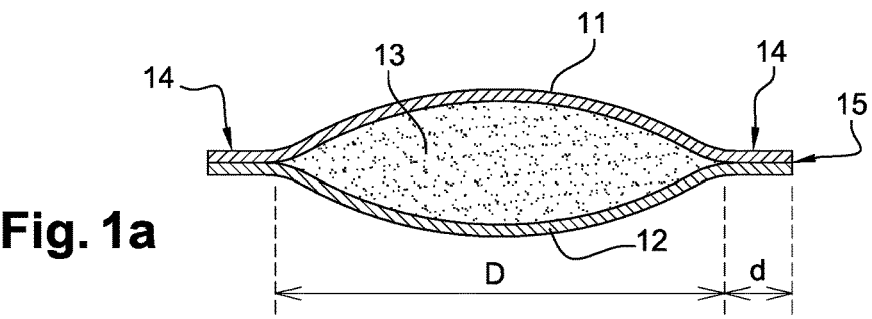
FIG. 1a is a cross-sectional view of of a packaging article, according to variouos embodiments of the present disclosure.

In the text hereinbelow, and unless otherwise indicated, the limits of a range of values are included within that range.

Within the meaning of the present invention and unless otherwise indicated:

the "aryl" or "heteroaryl" radicals or the aryl or heteroaryl part of a radical may be substituted with at least one substituent borne by a carbon atom, chosen from:

a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom, such as chlorine, fluorine or bromine;

a hydroxyl group;

a $C_1$-$C_2$ alkoxy radical;

a $C_2$-$C_4$ (poly)hydroxyalkoxy radical;

an amino radical;

nitro;

a 5- or 6-membered heterocycloalkyl radical;

an optionally cationic 5- or 6-membered heteroaryl radical, preferentially imidazolium, optionally substituted with a ($C_1$-$C_4$)alkyl radical, preferentially methyl;

an amino radical substituted with one or two identical or different $C_1$-$C_6$ alkyl radicals optionally bearing at least:
  i) one hydroxyl group,
  ii) one amino group optionally substituted with one or two optionally substituted $C_1$-$C_3$ alkyl radicals, the said alkyl radicals possibly forming, with the nitrogen atom to which they are attached, a saturated or unsaturated, optionally substituted 5- to 7-membered heterocycle, optionally comprising at least one other nitrogen or non-nitrogen heteroatom, an acylamino (—NR—C(O)R') radical in which the R radical is a hydrogen atom or a $C_1$-$C_4$ alkyl radical optionally bearing at least one hydroxyl group and the R' radical is a $C_1$-$C_2$ alkyl radical;

a carbamoyl ((R)$_2$N—C(O)—) radical in which the R radicals, which may be identical or different, represent a hydrogen atom or a $C_1$-$C_4$ alkyl radical optionally bearing at least one hydroxyl group;

a carboxylic acid or ester radical, (—O—C(O)R') or (—C(O)OR'), in which the radical R' is a hydrogen atom or a $C_1$-$C_4$ alkyl radical optionally bearing at least one hydroxyl group, and the radical R' is a $C_1$-$C_2$ alkyl radical;

the carboxylic radical possibly being in acid or salified form (preferably with an alkali metal or a substituted or unsubstituted ammonium);

an alkylsulfonylamino radical (R'SO$_2$—NR—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

an aminosulfonyl ((R)$_2$N—SO$_2$—) radical in which the R radicals, which may be identical or different, represent a hydrogen atom or a $C_1$-$C_4$ alkyl radical optionally bearing at least one hydroxyl group;

a cyano group (CN);

a (poly)haloalkyl group, preferably trifluoromethyl (CF$_3$);

the cyclic or heterocyclic part of a non-aromatic radical may be substituted with at least one substituent borne by a carbon atom, chosen from the groups:

hydroxyl, $C_1$-$C_4$ alkoxy or $C_2$-$C_4$ (poly)hydroxyalkoxy, alkylcarbonylamino ((RC(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy ((RC(O)—O—) in which the radical R is a $C_1$-$C_4$ alkyl radical or an amino radical substituted with two identical or different $C_1$-$C_4$ alkyl groups optionally bearing at least one hydroxyl group, the said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl ((RO—C(O)—) in which the radical R is a $C_1$-$C_4$ alkyl radical or an amino radical substituted with two identical or different $C_1$-$C_4$ alkyl groups optionally bearing at least one hydroxyl group, the said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical or a non-aromatic part of an aryl or heteroaryl radical may also be substituted with one or more oxo groups;

a "heterocycloalkyl radical" is a saturated heterocyclic radical;

a "cationic heteroaryl radical" is a heteroaryl group as defined above which comprises an endocyclic or exocyclic cationic group, when the charge is endocyclic, it is included in the electron delocalization via the mesomeric effect; for example, it is a pyridinium, imidazolium or indolinium group:

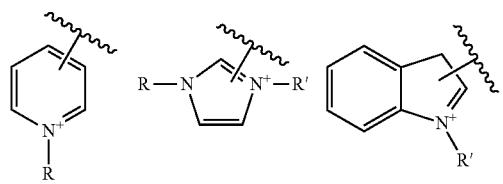

with R and R' being a heteroaryl substituent as defined previously and particularly a (hydroxy)($C_1$-$C_8$)alkyl group such as methyl;

when the charge is exocyclic, it is not included in the electron delocalization via the mesomeric effect; for example, it is an ammonium or phosphonium $R^+$ substituent, such as trimethylammonium, which is outside the heteroaryl, such as pyridyl, indolyl, imidazolyl or naphthalimidyl, in question:

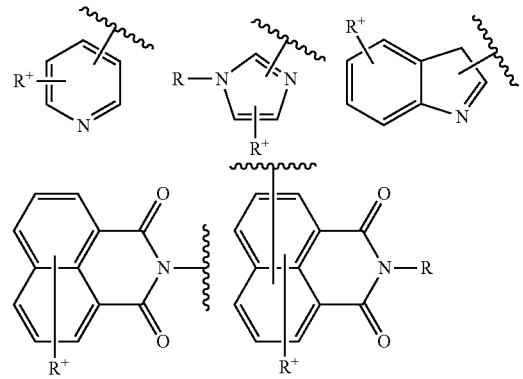

with R a heteroaryl substituent as defined previously and $R^+$ an ammonium $R_aR_bR_cN^+$—, phosphonium $R_aR_bR_cP^+$— or ammonium $R_aR_bR_cN^+$—($C_1$-$C_6$) alkylamino group with $R_a$, $R_b$ and $R_c$, which may be identical or different, representing a hydrogen atom or a ($C_1$-$C_8$)alkyl group such as methyl;

a "cationic aryl bearing an exocyclic charge" means an aryl ring whose cationic group is outside the said ring; it is especially an ammonium or phosphonium $R^+$ substituent such as trimethylammonium outside the aryl such as phenyl or naphthyl:

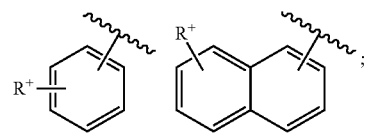

an "aryl" radical represents a monocyclic or fused or non-fused polycyclic group comprising from 6 to 22 carbon atoms, at least one ring of which is aromatic; the aryl radical is in particular a phenyl, biphenyl, naphthyl, indenyl, anthracenyl or tetrahydronaphthyl and more preferably phenyl;

a "heteroaryl" radical represents a 5- to 22-membered, monocyclic or fused or non-fused polycyclic group, comprising from 1 to 6 heteroatoms chosen from nitrogen, oxygen, sulfur and selenium atoms, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof;

a "cyclic" radical is a "cycloalkyl" radical, i.e. a non-aromatic monocyclic or fused or non-fused polycyclic radical containing from 5 to 22 carbon atoms, which may comprise one or more unsaturations, such as cyclohexyl or cyclopentyl;

a "heterocyclic" radical is a non-aromatic, monocyclic or fused or non-fused polycyclic 5- to 22-membered radical, comprising from 1 to 6 heteroatoms chosen from nitrogen, oxygen, sulfur and selenium atoms, morpholinyl, thiomorpholinyl, piperidyl, piperazinyl, pyrrolidinyl, tetrahydrofuryl, tetrahydrothiophenyl, azepanyl, thioazepanyl; preferentially pyrrolidinyl and morpholino;

an "alkyl" radical is a linear or branched $C_1$-$C_{16}$, preferably $C_1$-$C_8$ and particularly $C_1$-$C_4$ hydrocarbon-based radical, such as methyl or ethyl;

an "alkenyl" radical is a linear or branched $C_2$-$C_{20}$ hydrocarbon-based radical comprising one or more conjugated or unconjugated double bonds, in particular a $C_4$-$C_{10}$ radical comprising one, two or three double bonds, preferentially only one double bond;

the term "optionally substituted" attributed to the alkyl radical means that the said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming, with the nitrogen atom that bears them, a 5- to 7-membered heterocycle, optionally comprising another nitrogen or non-nitrogen heteroatom;

an "alkoxy" radical is an alkyl-oxy or alkyl-O— radical for which the alkyl radical is a linear or branched $C_1$-$C_{16}$ and preferentially $C_1$-$C_8$ hydrocarbon-based radical; particularly $C_1$-$C_4$ such as methoxy or ethoxy, and when the alkoxy group is optionally substituted, this means that the alkyl group is optionally substituted as defined above;

a "(poly)haloalkyl" radical is an "alkyl" radical as defined previously, in which one or more hydrogen atoms are substituted or replaced with one or more halogen atoms such as the fluorine, chlorine or bromine atom; a polyhaloalkyl that may be mentioned is the trifluoromethyl group;

an "alkylthio" radical is an alkyl-S— radical for which the alkyl radical is a linear or branched $C_1$-$C_{16}$ and preferentially $C_1$-$C_8$ hydrocarbon-based radical; particularly $C_1$-$C_4$ such as methylthio or ethylthio, and when the alkylthio group is optionally substituted, this means that the alkyl group is optionally substituted as defined above;

a cationic counterion is organic or mineral and preferentially chosen from alkali metal or alkaline-earth metal cations such as Na, Mg, K and Ca, and organic cations such as ammonium $NH_4^+$;

when the expression "at least one" is used, "one or more" is implied.

According to the present invention, the term "direct dye" means a compound which has the capacity of imparting colour and which is in the form of a coloured compound that may be observed with the naked eye, i.e. absorbing light at a wavelength in the visible range, at a wavelength $\lambda_{abs}$ in the visible spectrum between 400 and 700 nm.

A composition is said to be "anhydrous" when it comprises a water content of not more than 3% and preferably not more than 1% by weight relative to the weight of the composition. Preferably, this water content is not more than 0.5% by weight relative to the weight of the composition or powder. More particularly, the water content ranges from 0 to 1% by weight and preferably from 0 to 0.5% by weight relative to the total weight of the composition or powder.

The term "anhydrous paste" means an anhydrous composition with a viscosity of greater than 5 poises and preferably greater than 10 poises, measured at 25° C. and at a shear rate of 1 s$^{-1}$; this viscosity may be determined using a cone-plate rheometer.

The term "in anhydrous powder form" refers to an anhydrous composition or ingredient in pulverulent form, which is preferably substantially free of dust (or fine particles). In other words, the particle size distribution of the particles is such that the weight ratio of particles less than or equal to 100 micrometres in size (fines content) and preferably less than or equal to 65 micrometres in size (fines content) is advantageously less than or equal to 5%, preferably less than 2% and more particularly less than 1% (particle size evaluated using a Retsch AS 200 Digit particle size analyser; oscillation height: 1.25 mm/screening time: 5 minutes). Advantageously, the particle size is between 100 μm and 3 mm and more particularly between 65 μm and 2 mm.

According to a preferred embodiment of the invention, the dye composition comprising the direct dye(s) and optionally the chemical oxidizing agent are anhydrous in paste or powder form and are introduced into one or more cavities formed by the envelope.

The envelope may consist of a lap (e.g., ply or layer) consisting of water-soluble and/or liposoluble fibres and which is folded on itself, or alternatively the envelope may consist of a first lap that is covered with a second lap also consisting of water-soluble and/or liposoluble fibres. The lap folded on itself or the two laps are then hermetically assembled so that the pastes or powders cannot diffuse out, the pastes or powders thus being hermetically enveloped by the envelope i).

The term "water-soluble" means soluble in water, in particular in a proportion of at least 10 grams per litre of water, preferably at least 20 g/l and better still at least 50 g/l, at a temperature of less than or equal to 35° C.

The term "liposoluble" means soluble in a liquid fatty substance as defined below, in particular in a proportion of at least 10 grams per litre of liquid fatty substance, in particular in a plant oil or mineral oil such as liquid petroleum jelly, preferably at least 20 g/l in a liquid fatty substance, better still at least 50 g/l in a fatty substance, at a temperature of less than or equal to 35° C.

The term "temperature of less than or equal to 35° C." means a temperature not exceeding 35° C. and preferably greater than or equal to 0° C., for example ranging from more than 1.0° C. to 35° C., better still from 5° C. to 30° C. and even better still from 10° C. to 30° C. or 10° C. to 20° C. It is understood that all the temperatures are given at atmospheric pressure.

The packaging article according to the invention is preferably water-soluble or liposoluble at a temperature of less than or equal to 35° C.

i) An Envelope Comprising Water-soluble and/or Liposoluble Fibres

The packaging article according to the invention comprises an envelope which defines at least one cavity, the cavity(ies) containing at least one anhydrous dye composition containing at least one direct dye, the packaging article optionally containing at least one chemical oxidizing agent in one of its cavities. The packaging article preferably comprises only one cavity.

The envelope of the present invention comprises one or more laps of water-soluble and/or liposoluble fibres and one or more cavities containing the anhydrous dye composition, the dye composition being separate from the lap or from the envelope. Such an envelope is different from water-soluble or liposoluble thin films in which the dye composition would be incorporated in the lap(s) forming the envelope. Relative to these water-soluble or liposoluble thin films, the envelope according to the invention has the advantage of allowing the incorporation of constituents that are incompatible therewith, and of being simpler to use since it does not require any premixing or any dissolution in a solvent of the constituents, or any heating to evaporate the solvent. The process for manufacturing the packaging article of the invention is also faster and less expensive than the process for manufacturing thin films.

Furthermore, when the active agents, in this case in particular the dyes, are used in dispersion to form a thin film, this may give rise to compatibility problems and mechanical problems (breaking of the film) and may impose limits on the concentration of active agents. In addition, the envelope and the laps that are useful for the invention have the advantage of allowing wider diversity in the choice of the shape and appearance of the article, since the water-soluble and/or liposoluble lap(s) may have a variable thickness and a variable density, giving access to a wide variety of shapes and sizes, whereas the thin film is difficult to dry if the thickness is too large, and it is fragile and difficult to manipulate if the size is too large.

Advantageously, the envelope or the laps are "touch-deformable", which especially means that the envelope and the laps become deformed when they are held and pinched between a user's fingers.

Preferably, the anhydrous dye composition in powder or paste form and optionally the anhydrous oxidizing agent(s) in powder or paste form are present in a cavity generated by at least two laps constituting the envelope and defining between them a cavity, the said laps preferably comprising water-soluble fibres.

According to a particular embodiment of the invention, at least one of the laps of the packaging article consists exclusively of water-soluble fibres, and more preferentially all the laps of the packaging article of the invention consist exclusively of water-soluble fibres, preferably water-soluble at a temperature of less than or equal to 30° C.

The term "fibre" means any object whose length is greater than its cross section. In other words, it should be understood as meaning an object of length L and of diameter D such that L is greater and preferably very much greater (i.e. at least three times greater) than D, D being the diameter of the circle in which the cross section of the fibre is inscribed. In particular, the ratio L/D (or aspect ratio) is chosen in the range from 3.5 to 2500, preferably from 5 to 500 and better still from 5 to 150. The cross section of a fibre may have any round, toothed or fluted shape, or alternatively a bean shape, but also multilobate, in particular trilobate or pentalobate, X-shaped, ribbon-shaped, square, triangular, elliptical or the like. The fibres of the invention may or may not be hollow. The fibres used according to the present invention may be of natural, synthetic or even artificial origin. Advantageously, the said fibres are of synthetic origin.

A "natural fibre" is by definition a fibre that is naturally present in nature, directly or after mechanical and/or physical treatment. Fibres of animal origin, cellulose fibres, in particular extracted from wood, plants or algae, and rayon fibres, are collated in this category.

The "artificial fibres" are either totally synthetic or derived from natural fibres that have been subjected to one or more chemical treatments in order especially to improve their mechanical and/or physicochemical properties.

The "synthetic fibres" collate fibres obtained by chemical synthesis and are generally fibres consisting of one or more mono-component or multi-component, composite or non-composite polymers and/or copolymers, which are generally extruded and/or drawn to the desired diameter of the fibre.

Preferably, the fibres of the invention consist of one or more water-soluble polymers.

The water-soluble polymer(s) of the invention contain in their backbones water-soluble units. The water-soluble units are obtained from one or more water-soluble monomers.

The term "water-soluble monomer" means a monomer whose solubility in water is greater than or equal to 1% and preferably greater than or equal to 5% at 25° C. and at atmospheric pressure (760 mmHg).

The said synthetic water-soluble polymer(s) used in the context of the present invention are advantageously obtained from water-soluble monomers comprising at least one double bond. These monomers may be chosen from cationic, anionic and nonionic monomers, and mixtures thereof.

As water-soluble monomers that may be used as precursors of the water-soluble units, alone or as a mixture, examples that may be mentioned include the following monomers, which may be in free or salified form:

(meth)acrylic acid,
styrenesulfonic acid,
vinyl sulfonic acid and (meth)allylsulfonic acid,
vinylphosphonic acid,
N-vinylacetamide and N-methyl-N-vinylacetamide,
N-vinylformamide and N-methyl-N-vinylformamide,
N-vinyllactams comprising a cyclic alkyl group containing from 4 to 9 carbon atoms, such as N-vinylpyrrolidone, N-butyrolactam and N-vinylcaprolactam,
maleic anhydride,
itaconic acid,
vinyl alcohol of formula $CH_2=CHOH$,
vinyl ethers of formula $CH_2=CHOR$ in which R is a linear or branched, saturated or unsaturated hydrocarbon-based radical containing from 1 to 6 carbons,
dimethyldiallylammonium halides (chloride),
quaternized dimethylaminoethyl methacrylate (DMAEMA),
(meth)acrylamidopropyltrimethylammonium halides (chloride) (APTAC and MAPTAC),
methylvinylimidazolium halides (chloride),
2-vinylpyridine and 4-vinylpyridine,
acrylonitrile,
glycidyl (meth)acrylate,
vinyl halides (chloride) and vinylidene chloride,
vinyl monomers of formula (I) below:

$$H_2C=C(R)-C(O)-X \qquad (I)$$

in which formula (I):
R is chosen from H and $(C_1-C_6)$alkyl such as methyl, ethyl and propyl;
X is chosen from:
alkoxy of —OR' type in which R' is a linear or branched, saturated or unsaturated hydrocarbon-based radical containing from 1 to 6 carbon atoms, optionally substituted with at least one halogen atom (iodine, bromine, chlorine or fluorine); a sulfonic ($—SO_3^-$), sulfate ($—SO_4^-$), phosphate ($—PO_4H_2$); hydroxyl (—OH); primary amine ($—NH_2$); secondary amine ($—NHR_6$), tertiary amine ($—NR_6R_7$) or quaternary amine ($—N^+R_6R_7R_8$) group with $R_6$, $R_7$ and $R_8$ being, independently of each other, a linear or branched, saturated or unsaturated hydrocarbon-based radical containing 1 to 6 carbon atoms, with the proviso that the sum of the carbon atoms of $R'+R_6+R_7+R_8$ does not exceed 6;

groups —NH$_2$, —NHR' and —NR'R" in which R' and R" are, independently of each other, linear or branched, saturated or unsaturated hydrocarbon-based radicals containing 1 to 6 carbon atoms, with the proviso that the total number of carbon atoms of R'+R" does not exceed 6, the said R' and R" being optionally substituted with one halogen atom (iodine, bromine, chlorine or fluorine); a hydroxy (—OH); sulfonic (—SO$_3^-$), sulfate (—SO$_4^-$), phosphate (—PO$_4$H$_2$); primary amine (—NH$_2$); secondary amine (—NHR$_6$), tertiary amine (—NR$_6$R$_7$) and/or quaternary amine (—N$^+$R$_6$R$_7$R$_8$) group with R$_6$, R$_7$ and R$_8$ being, independently of each other, a linear or branched, saturated or unsaturated hydrocarbon-based radical containing 1 to 6 carbon atoms, with the proviso that the sum of the carbon atoms of R'+R"+R$_6$+R$_7$+R$_8$ does not exceed 6.

As compounds corresponding to this formula, examples that may be mentioned include N,N-dimethylacrylamide and N,N-diethylacrylamide; and mixtures thereof.

Anionic monomers that may especially be mentioned include (meth)acrylic acid, acrylamido-2-methylpropanesulfonic acid, itaconic acid and alkali metal, alkaline-earth metal or ammonium salts thereof or salts thereof derived from an organic amine such as an alkanolamine.

Nonionic monomers that may especially be mentioned include (meth)acrylamide, N-vinylformamide, N-vinylacetamide, hydroxypropyl (meth)acrylate and the vinyl alcohol of formula CH$_2$=CHOH.

The cationic monomers are preferably chosen from quaternary ammonium salts derived from a diallylamine and those corresponding to formula (II) below:

in which formula (II):
R$_1$ represents a hydrogen atom or a methyl group,
R$_2$ and R$_3$, which may be identical or different, represent a hydrogen atom or a linear or branched C$_1$-C$_4$ alkyl group,
R$_4$ represents a hydrogen atom or a linear or branched C$_1$-C$_4$ alkyl group or an aryl group,
D represents the following divalent unit: —(Y)$_n$-(A)- in which:
Y represents an amide function, an ester (O—C(O) or C(O)—O), a urethane or a urea,
A represents a linear or branched, cyclic or acyclic C$_1$-C$_{10}$ alkylene group, which may be substituted or interrupted with a divalent aromatic or heteroaromatic group. The alkylene groups may be interrupted with an oxygen atom, a nitrogen atom, a sulfur atom or a phosphorus atom; the alkylene may be interrupted with a ketone function, an amide, an ester (O—C(O) or C(O)—O), a urethane or a urea,
n is an integer ranging from 0 to 1,
X$^-$ represents an anionic counterion, for instance a chloride or a sulfate.

Examples of water-soluble cationic monomers that may especially be mentioned include the following compounds, and also salts thereof: dimethylaminoethyl, (meth)acryloyloxyethyltrimethylammonium, (meth)acryloyloxyethyldimethylbenzylammonium, N-[dimethylaminopropyl](meth)acrylamide, (meth)acrylamidopropyltrimethylammonium, (meth)acrylamidopropyldimethylbenzylammonium, dimethylaminohydroxypropryl, (meth)acryloyloxyhydroxypropyltrimethylammonium, (meth)acryloyloxyhydroxypropyldimethylbenzylammonium and dimethyldiallylammonium (meth)acrylate.

Preferably, the polymer according to the invention is polymerized from at least one cationic monomer as defined above.

Preferably, the polymers are polymerized from the following monomers comprising at least one double bond as follows:
0 to 30 mol % of acrylic acid,
0 to 95.5 mol % of acrylamide, and
0.5 mol % to 100 mol % of at least one cationic monomer represented in formula (II) as defined above.

As polymers that are particularly preferred in the invention, mention may be made especially of those polymerized from:
10% of acryloyloxyethyldimethylbenzylammonium chloride and 90% of acrylamide,
30% of acryloyloxytrimethylammonium chloride, 50% of acryloyloxyethyldimethylbenzylammonium chloride and 20% of acrylamide,
10% of acryloyloxyethyltrimethylammonium chloride and 90% of acrylamide,
30% of diallyldimethylammonium chloride and 70% of acrylamide,
30% of acrylic acid and 70% of acrylamide.

According to a particular embodiment, the polymers are polymerized from a cationic monomer and acrylic acid, the number of moles of the cationic monomer being greater than the number of moles of acrylic acid.

As water-soluble polymers derived from natural products, mention may be made of polysaccharides, i.e. polymers bearing a sugar unit or sugar units.

The term "sugar unit" means a unit derived from a carbohydrate of formula C$_n$(H$_2$O)$_{n-1}$ or (CH$_2$O)$_n$, which may be optionally modified by substitution and/or by oxidation and/or by dehydration. The sugar units that may be included in the composition of the polymers of the invention are preferably derived from the following sugars: glucose, galactose, arabinose, rhamnose, mannose, xylose, fucose, fructose, anhydrogalactose, galacturonic acid, glucuronic acid, mannuronic acid, galactose sulfate or anhydrogalactose sulfate.

The polymers bearing a sugar unit or sugar units according to the invention may be of natural or synthetic origin. They may be nonionic, anionic, amphoteric or cationic. The base units of the polymers bearing a sugar unit of the invention may be monosaccharides or disaccharides.

As polymers that may be used, mention may be made especially of the following native gums, and also derivatives thereof:
a) tree or shrub exudates, including:
gum arabic (branched polymer of galactose, arabinose, rhamnose and glucuronic acid);
ghatti gum (polymer derived from arabinose, galactose, mannose, xylose and glucuronic acid);
karaya gum (polymer derived from galacturonic acid, galactose, rhamnose and glucuronic acid);
gum tragacanth (or tragacanth) (polymer of galacturonic acid, galactose, fucose, xylose and arabinose);
b) gums derived from algae, including:
agar (polymer derived from galactose and anhydrogalactose);
alginates (polymers of mannuronic acid and of glucuronic acid);
carrageenans and furcellerans (polymers of galactose sulfate and of anhydrogalactose sulfate);
c) gums derived from seeds or tubers, including:
guar gum (polymer of mannose and galactose);
locust bean gum (polymer of mannose and galactose);

fenugreek gum (polymer of mannose and galactose);
tamarind gum (polymer of galactose, xylose and glucose);
konjac gum (polymer of glucose and mannose) in which the main constituent is glucomannan, a polysaccharide of high molecular weight ($500\,000 < M_{glucomannan} < 2\,000\,000$) composed of D-mannose and D-glucose units with a branch every 50 or 60 units approximately;

d) microbial gums, including:
xanthan gum (polymer of glucose, mannose acetate, mannose/pyruvic acid and glucuronic acid);
gellan gum (polymer of partially acylated glucose, rhamnose and glucuronic acid);
scleroglucan gum (glucose polymer);
biosaccharide gum (polymer of galacturonic acid, fucose and D-galactose), for example the product sold under the name Fucogel 1.5P from Solabia (polysaccharide rich in fucose (20%) at 1.1% in water and stabilized (1.5% phenoxyethanol));

e) plant extracts, including:
cellulose (glucose polymer);
starch (glucose polymer);
inulin (polymer of fructose and glucose).

These polymers may be physically or chemically modified. A physical treatment that may especially be mentioned is the temperature. Chemical treatments that may be mentioned include esterification, etherification, amidation or oxidation reactions. These treatments can lead to polymers that may be nonionic, anionic, cationic or amphoteric.

Preferably, these chemical or physical treatments are applied to guar gums, locust bean gums, starches and celluloses.

The nonionic guar gums that may be used according to the invention may be modified with $C_1$-$C_6$ hydroxyalkyl groups. Among the hydroxyalkyl groups that may be mentioned are hydroxymethyl, hydroxyethyl, hydroxypropyl and hydroxybutyl groups.

These guar gums are well known in the prior art and may be prepared, for example, by reacting the corresponding alkene oxides, for instance propylene oxides, with the guar gum so as to obtain a guar gum modified with hydroxypropyl groups.

The degree of hydroxyalkylation preferably ranges from 0.4 to 1.2, and corresponds to the number of alkylene oxide molecules consumed by the number of free hydroxyl functions present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The guar gums modified with cationic groups that may be used more particularly according to the invention are guar gums comprising trialkylammonium cationic groups. Preferably, 2% to 30% by number of the hydroxyl functions of these guar gums bear trialkylammonium cationic groups. Even more preferentially, 5% to 20% by number of the hydroxyl functions of these guar gums are branched with trialkylammonium cationic groups. Among these trialkylammonium groups, mention may be made most particularly of trimethylammonium and triethylammonium groups. Even more preferentially, these groups represent from 5% to 20% by weight relative to the total weight of the modified guar gum.

According to the invention, use may be made of guar gums modified with 2,3-epoxypropyltrimethylammonium chloride.

These guar gums modified with cationic groups are products already known per se and are, for example, described in patents U.S. Pat. Nos. 3,589,578 and 4,0131,307. Such products are moreover sold especially under the trade names Jaguar C13 S, Jaguar C 15 and Jaguar C 17 by the company Rhodia Chimie.

A modified locust bean gum that may be used is cationic locust bean gum containing hydroxypropyltrimonium groups, such as Catinal CLB 200 sold by the company Toho.

The starch molecules used in the present invention may originate from any plant source of starch, especially cereals and tubers; more particularly, they may be starches from corn, rice, cassava, barley, potato, wheat, sorghum, pea, oat or tapioca. It is also possible to use the starch hydrolysates mentioned above. The starch is preferably derived from potato.

The starches may be chemically or physically modified, especially by one or more of the following reactions: pregelatinization, oxidation, crosslinking, esterification, etherification, amidation and heat treatments.

More particularly, these reactions may be performed in the following manner:
pregelatinization by splitting the starch granules (for example drying and cooking in a drying drum);
oxidation with strong oxidizing agents, leading to the introduction of carboxyl groups into the starch molecule and to depolymerization of the starch molecule (for example by treating an aqueous starch solution with sodium hypochlorite);
crosslinking with functional agents capable of reacting with the hydroxyl groups of the starch molecules, which will thus bond together (for example with glyceryl and/or phosphate groups);
esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type Am—O—PO—$(OX)_2$), distarch phosphates (of the type Am—O—PO—(OX)—O—Am) or even tristarch phosphates (of the type Am—O—PO—(O—Am)$_2$) or mixtures thereof may especially be obtained by crosslinking with phosphorus compounds, Am meaning starch and X especially denoting alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure *Zea* from National Starch (gelatinized corn distarch phosphate).

A preferred starch is a starch that has undergone at least one chemical modification such as at least one esterification.

According to the invention, amphoteric starches comprising one or more anionic groups and one or more cationic groups may also be used. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds having the following formulae:

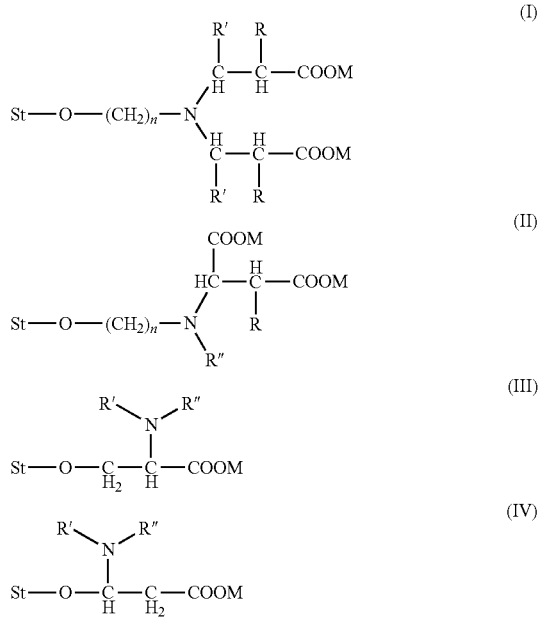

in which formulae (I) to (IV):

St—O represents a starch molecule;

R, which may be identical or different, represents a hydrogen atom or a methyl radical;

R', which may be identical or different, represents a hydrogen atom, a methyl radical or a group —C(O)—OH;

n is an integer equal to 2 or 3;

M, which may be identical or different, denotes a hydrogen atom, an alkali metal or alkaline-earth metal such as Na, K or Li, a quaternary ammonium $NH_4$, or an organic amine, R" represents a hydrogen atom or a $C_1$-$C_{18}$ alkyl radical.

These compounds are especially described in U.S. Pat. Nos. 5,455,340 and 4,017,460.

Use is particularly made of the starches of formula (II) or (III); and preferentially starches modified with 2-chloroethylaminodipropionic acid, i.e. starches of formula (II) or (III) in which R, R', R" and M represent a hydrogen atom and n is equal to 2. The preferred amphoteric starch is a starch chloroethylamidodipropionate.

The celluloses and cellulose derivatives may be anionic, cationic, amphoteric or nonionic.

Among these derivatives, cellulose ethers, cellulose esters and cellulose ester ethers are distinguished.

Among the cellulose esters, mention may be made of mineral cellulose esters (cellulose nitrates, sulfates and phosphates), organic cellulose esters (cellulose monoacetates, triacetates, amidopropionates, acetate butyrates, acetate propionates and acetate trimellitates), and mixed organic/mineral cellulose esters, such as cellulose acetate butyrate sulfates and cellulose acetate propionate sulfates.

Among the cellulose ester ethers, mention may be made of hydroxypropylmethylcellulose phthalates and ethylcellulose sulfates.

Among the nonionic cellulose ethers that may be mentioned are alkylcelluloses such as methylcelluloses and ethylcelluloses (for example Ethocel Standard 100 Premium from Dow Chemical); hydroxyalkylcelluloses such as hydroxymethylcelluloses and hydroxyethylcelluloses (for example Natrosol 250 HHR sold by Aqualon) and hydroxypropylcelluloses (for example Klucel EF from Aqualon); mixed hydroxyalkyl-alkylcelluloses such as hydroxypropylmethylcelluloses (for example Methocel E4M from Dow Chemical), hydroxyethylmethylcelluloses, hydroxyethylethylcelluloses (for example Bermocoll E 481 FQ from Akzo Nobel) and hydroxybutylmethylcelluloses.

Among the anionic cellulose ethers, mention may be made of carboxyalkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and also the sodium salts thereof.

Among the cationic cellulose ethers, mention may be made of crosslinked or non-crosslinked, quaternized hydroxyethylcelluloses. The quaternizing agent may especially be diallyldimethylammonium chloride (for example Celquat L200 from National Starch). Another cationic cellulose ether that may be mentioned is hydroxypropyltrimethylammonium hydroxyethyl cellulose (for example Ucare Polymer JR 400 from Amerchol).

Among the associative polymers bearing a sugar unit or sugar units, mention may be made of celluloses or derivatives thereof, modified with groups comprising at least one fatty chain, such as alkyl, arylalkyl or alkylaryl groups or mixtures thereof in which the alkyl groups are of C8-C22; nonionic alkylhydroxyethylcelluloses such as the products Natrosol Plus Grade 330 CS and Polysurf 67 ($C_{16}$ alkyl) sold by the company Aqualon; quaternized alkylhydroxyethylcelluloses (cationic), such as the products Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) sold by the company Amerchol, the products Crodacel QM and Crodacel QL ($C_{12}$ alkyl) and Crodacel QS ($C_{18}$ alkyl) sold by the company Croda, and the product Softcat SL 100 sold by the company Amerchol; nonionic nonoxynylhydroxyethylcelluloses such as the product Amercell HM-1500 sold by the company Amerchol; nonionic alkylcelluloses such as the product Bermocoll EHM 100 sold by the company Berol Nobel.

As associative polymers bearing a sugar unit or sugar units derived from guar, mention may be made of hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

The polymer(s) bearing a sugar unit or sugar units of the invention are preferably chosen from guar gums, locust bean gums, xanthan gums, starches and celluloses, in their modified form (derivatives) or unmodified.

Preferably, the polymers bearing a sugar unit or sugar units according to the invention are nonionic.

More preferably, the polymer(s) bearing a sugar unit or sugar units of the invention are chosen from modified nonionic guar gums, especially modified with $C_1$-$C_6$ hydroxyalkyl groups.

The polymers described above more particularly have a weight-average molecular weight of greater than 1 000 000 and preferably between 1 000 000 and 50 000 000. The molecular weight is determined by the RSV (Reduced Specific Viscosity) method as defined in "Principles of Polymer Chemistry" Cornell University Press, Ithaca, N.Y. 1953 Chapter VII "Determination of molecular weight" pp. 266-316.

The fibres may be spun, carded or twisted. Advantageously, the fibres used in the context of the present invention are spun. The mean diameter of the fibres used according to the present invention, which may be identical or different, is less than 500 μm. Advantageously, such a diameter is less than 200 μm, preferably less than 100 μm or even less than 50 μm.

Mention may be made more particularly of water-soluble fibres that include fibres based on polyvinyl alcohol PVA, fibres of polysaccharides such as glucomannans, starches or celluloses such as carboxymethylcelluloses, polyalginic acid fibres, polylactic acid fibres and polyalkylene oxide fibres, and also mixtures thereof. More preferentially, the water-soluble fibre(s) used in the invention are chosen from PVA-based fibres.

More particularly the envelope i) comprises natural, artificial or synthetic water-soluble polymer fibres, preferably chosen from polyvinyl alcohol (PVA) fibres, polysaccharide fibres such as cellulose and more specifically hydroxyalkylcelluloses, polylactic acid fibres and polyalkylene oxide fibres, and mixtures thereof; more preferably selected from PVA and hydroxyl($C_1$-$C_6$)alkylcelluloses.

The fibres of the envelope or of the laps are generally entangled. As indicated above, the term "envelope or lap comprising water-soluble fibres" means an envelope or laps which may consist entirely of water-soluble fibres or a lap which may comprise both water-soluble fibres and fibres that are insoluble in water at a temperature of less than or equal to 35° C., the soluble fibres necessarily being in a larger amount than the insoluble fibres. The lap of fibres should comprise at least 60% by weight, preferably at least 70% and better still at least 80% by weight of soluble fibres relative to the total weight of fibres. It may thus comprise, for example, more than 95% by weight, or even more than 99% by weight and even 100% by weight of water-soluble fibres relative to the total weight of fibres in the envelope or the laps.

When the lap of fibres contains insoluble fibres, the latter fibres may be made of any material usually used as insoluble fibres; they may be, for example, silk fibre, cotton fibre, wool fibre, flax fibre, polyamide (Nylon®) fibre, polylactic acid fibre, modified cellulose (rayon, viscose or rayon acetate) fibre, poly-p-phenyleneterephthalamide fibre, especially Kevlar® fibre, polyolefin fibre and especially polyethylene or polypropylene fibre, glass fibre, silica fibre, aramid fibre, carbon fibre, especially in graphite form, Teflon® fibre, insoluble collagen fibre, polyester fibre, polyvinyl or polyvinylidene chloride fibre, polyethylene terephthalate fibre, and fibres formed from a mixture of the compounds mentioned above, for instance polyamide/polyester or viscose/polyester fibres.

In addition, the envelope and the laps of the invention may be woven or nonwoven.

According to a particular embodiment, the envelope and the laps of the invention are woven. In the context of the present invention, a "woven" results from an organized assembly of fibres, in particular of water-soluble polymeric fibres, and more particularly of an intercrossing, in the same plane, of the said fibres, arranged in the warp direction and of fibres arranged perpendicular to the warp fibres, in the weft direction. The binding obtained between these warp and weft fibres is defined by a weave.

Such a woven material results from an operation directed towards assembling the fibres in an organized manner such as weaving per se, but may also result from knitting.

More particularly, the two layers or laps comprising the woven polymeric water-soluble fibres that constitute the envelope of the packaging article of the invention do not comprise any other additional layer superposed thereon.

According to another particularly advantageous mode of the invention, the envelope and the laps are nonwoven.

Nonwovens are described in general in Riedel's *Nonwoven Bonding Methods & Materials*, Nonwoven World (1987), which is incorporated herein by reference.

For the purposes of the present invention, the expression "nonwoven" means a substrate comprising fibres, in particular water-soluble polymeric fibres, in which substrate the individual fibres are arranged in a disordered manner in a structure in the form of a lap and which are neither woven nor knitted. The fibres of the nonwoven are generally bonded together, either under the effect of a mechanical action (for example needle punching, air jet, water jet, etc.), or under the effect of a thermal action, or by addition of a binder.

Such a nonwoven is, for example, defined by standard ISO 9092 as a web or lap of directionally or randomly orientated fibres, bonded by friction and/or cohesion and/or adhesion, excluding paper and products obtained by weaving, knitting, tufting or stitching incorporating binding yarns or filaments.

A nonwoven differs from a paper by virtue of the length of the fibres used. In paper, the fibres are shorter. However, nonwovens exist based on cellulose fibre, which are manufactured by a wet-laid process and which have short fibres as in paper. The difference between a nonwoven and a paper is generally the absence of hydrogen bonding between the fibres in a nonwoven.

Very preferentially, the fibres used in the context of the present invention are chosen from synthetic fibres such as PVA fibres. In particular, the envelope and laps of the invention are nonwoven, and preferentially made of nonwoven PVA fibres.

To produce the nonwoven water-soluble lap(s) of the envelope of the packaging article, use is preferably made of PVA fibres that are soluble in water at a temperature of less than or equal to 35° C., for instance the fibres sold by the Japanese company Kuraray under the name Kuralon K-II, and particularly the grade WN2 which is soluble at and above 20° C. These fibres are described in document EP-A-636 716 which teaches the manufacture of PVA fibres that are soluble in water at temperatures not exceeding 100° C., by spinning and drawing the polyvinyl alcohol polymer in dry or wet form in the presence of solvents participating in the dissolution and solidification of the fibre. The fibre thus obtained may lead to the production of woven or nonwoven substrates. According to a particular mode of the invention, the PVA fibres of the examples of EP-A-636 716 are used, especially Example 2 and Comparative Example 1: commercial product Solvron SS.

These fibres may also be prepared from a solution to be spun, by dissolving a water-soluble PVA-based polymer in a first organic solvent, spinning the solution in a second organic solvent to obtain solidified filaments and wet-drawing of the filaments from which the first solvent is removed, and which are then dried and subjected to a heat treatment. The cross section of these fibres may be substantially circular. These fibres have a tensile strength of at least 2.7 g/dtex (3 g/d). Patent application EP-A-0 636 716 describes such PVA-based water-soluble fibres and the process for manufacturing them. For example, the fibres may also be formed by extrusion and deposited on a conveyor to form a lap of fibres which is then consolidated via a standard fibre bonding technique, for instance needle punching, hot-bonding, calendering or air-through bonding, in which technique the water-soluble lap passes through a tunnel in which hot air is blown, or hydroentanglement directed towards bonding the fibres via the action of fine jets of water at very high pressure, which cannot be applied to fibres whose dissolution temperature is too low pressure.

As has been seen previously, the invention is not limited to the use of PVA, and use may also be made of fibres made of other water-soluble materials, provided that these materials dissolve in water at the desired temperature, for example the polysaccharide fibres sold under the name Lysorb by the company Lysac Technologies, Inc. or other fibres based on polysaccharide polymers such as glucomannans or starch.

The laps of the envelope may comprise a mixture of different fibres that are soluble in water at various temperatures (up to 35° C.).

The fibres may be composite, and they may comprise, for example, a core and a sheath not having the same nature, for example formed from different grades of PVA.

According to a particular embodiment of the invention, the lap(s) of the envelope are a nonwoven comprising water-soluble fibres, alone or as a mixture with insoluble fibres as indicated above, with not more than 40% by weight of insoluble fibres relative to the total weight of the fibres constituting the lap. Preferably, the nonwoven consists essentially of water-soluble fibres, i.e. it does not contain any insoluble fibres.

The envelope may have any shape that is suitable for the intended use, for example a rectangular, circular or oval shape, and it preferably has dimensions that enable it to be held between at least two fingers. Thus, the envelope or the laps may have, for example, an ovoid shape from about 2 to 10 cm long and from about 0.5 to 4 cm wide, or a circular disc shape from about 2 to 10 cm in diameter, or a square shape with a side length from about 5 to 15 cm, or a rectangular shape with a length from about 5 to 25 cm, it being understood that it may have any other shape and size that are suitable for the desired use.

Advantageously, the envelope and the laps have a low thickness, the laps possibly consisting of several layers. Preferably, the thickness of the envelope and of the laps ranges from 3% to 99.9% of its other dimensions. This thickness is especially less than 100 mm. The envelope and the laps are thus substantially flat, thin slices.

The surface delimiting the cavity(ies) has an area generally less than 625 cm$^2$, for example between 400 cm$^2$ and 0.025 cm$^2$.

Use may be made, for example, of an envelope and laps as defined in French patent application FR 12/61120 deposited on 22 Nov. 2012 by the Applicant.

The article according to the present invention may comprise one or more water-soluble nonwoven laps and envelope.

Preferentially, the amount of envelope present in the article according to the invention is inclusively between 0.5% and 20.0% by weight relative to the total weight of the said article, advantageously inclusively between 1.0% and 10.0%, particularly inclusively between 2.0% and 5.0% and more particularly 3% by weight relative to the total weight of the packaging article.

FIG. 1a) is a cross section of a particular embodiment of the packaging article comprising the envelope i) consisting of two laps, which are preferably water-soluble, 11 and 12, bonded together in a peripheral region 14. Preferably, the two laps are joined by any suitable fixing means such as glueing, welding, especially heat-welding, and in particular by entanglement. The first lap 11 also has a free central region D arranged facing a free central region D of the second lap 12. These two central regions delimit a central cavity, the said cavity containing an anhydrous dye composition 13 as defined previously comprising at least one direct dye optionally mixed with other powdered ingredients.

The laps 11 and 12 have a closed outer perimeter 15. The shape of the outer perimeter 15 is, for example, rounded, such as circular or elliptical, or polygonal, such as square, rectangular or triangular, preferably circular.

Figure 1B:
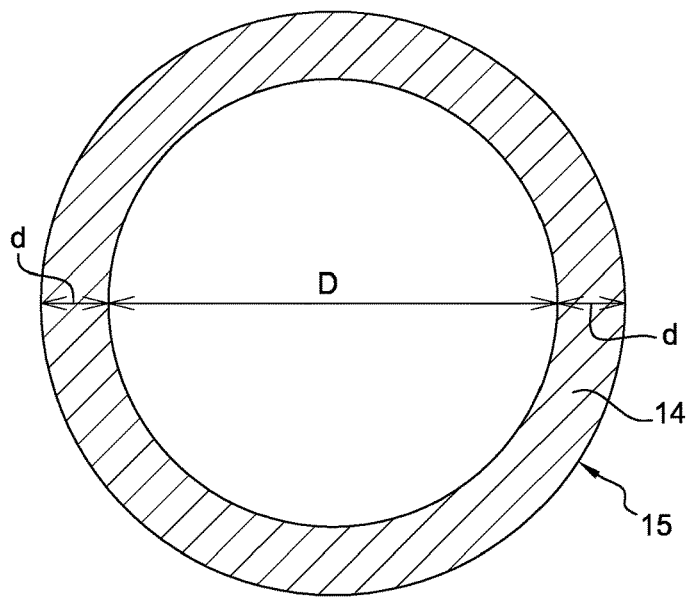

FIG. 1b) shows a top view of the packaging article as described in FIG. 1a), in which part D corresponds to the cavity or "central region" in which is found the anhydrous dye composition 13, and d corresponds to the peripheral region hermetically joining the two laps 11 and 12.

Figure 1C:
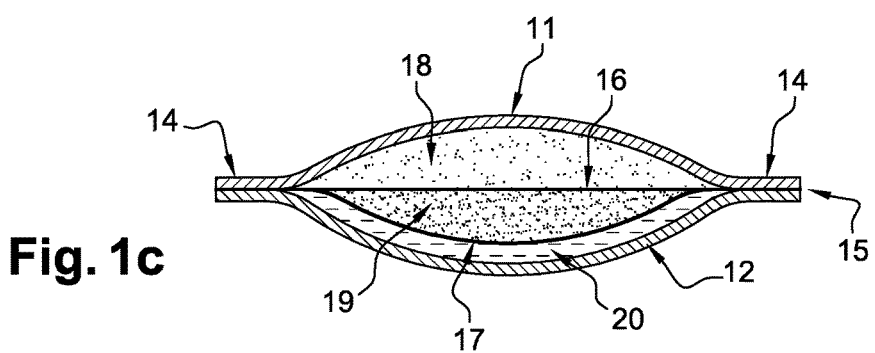
FIG. 1c is a cross-sectional view of of a packaging article, according to various embodiments of the present disclosure.

FIG. 1c) shows a cross section of a particular embodiment of the packaging article, comprising an envelope consisting of two laps 11 and 12, which are preferably water-soluble, and comprising an additional lap 16, which is preferably water-soluble, and optionally other additional laps 17, which are preferably water-soluble, which define several cavities in which are housed the ingredients such as the anhydrous dye composition as defined previously comprising at least one direct dye 18, chemical oxidizing agents and/or other dyes other than the direct dyes 19 or the powdered persalts 20 as defined below.

The first lap 11 has a thickness smaller than its other dimensions, for example less than 10% of its maximum transverse dimension D+2d.

The thickness of the first lap 11 is, for example, less than 10 mm and especially between 0.1 mm and 3 mm. Its maximum transverse dimension D+d is, for example, less than 100 mm, and is especially inclusively between 10 mm and 60 mm.

The first lap 11 thus forms a layer, for example made of nonwoven, which itself may consist of several layers of nonwoven that are consolidated together.

The second lap 12 also has a closed outer perimeter 15. The outer perimeter 15 of the first lap 11 has a shape substantially identical to the outer perimeter 15 of the second lap 12.

The second lap 12 has a thickness smaller than its other dimensions, for example less than 10% of its maximum transverse dimension D+2d.

The thickness of the second lap 12, which is preferably water-soluble, is, for example, less than 10 mm and especially between 0.1 mm and 3 mm. Its maximum transverse dimension D+2d is less than 100 mm, and is especially between 10 mm and 60 mm.

The thickness is advantageously measured according to the standard EDANA WSP 120.1(5).

The second lap 12 is advantageously a nonwoven.

The first lap 11 and the second lap 12, which may be identical or of different thicknesses, densities and/or compositions, are preferably nonwovens that are water-soluble at a temperature of less than or equal to 35° C. The laps and nonwoven envelope are soluble in an aqueous solution, such as water. The nonwoven laps and envelope are preferentially made of PVA.

Figure 1D:
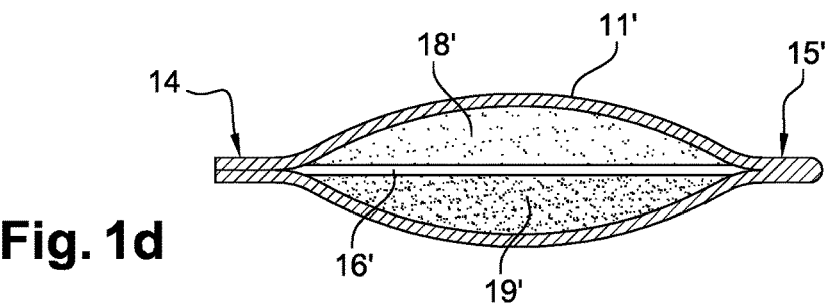
FIG. 1d is a cross-sectional view of of a packaging article, according to various embodiments of the present disclosure.
Figure 1E:
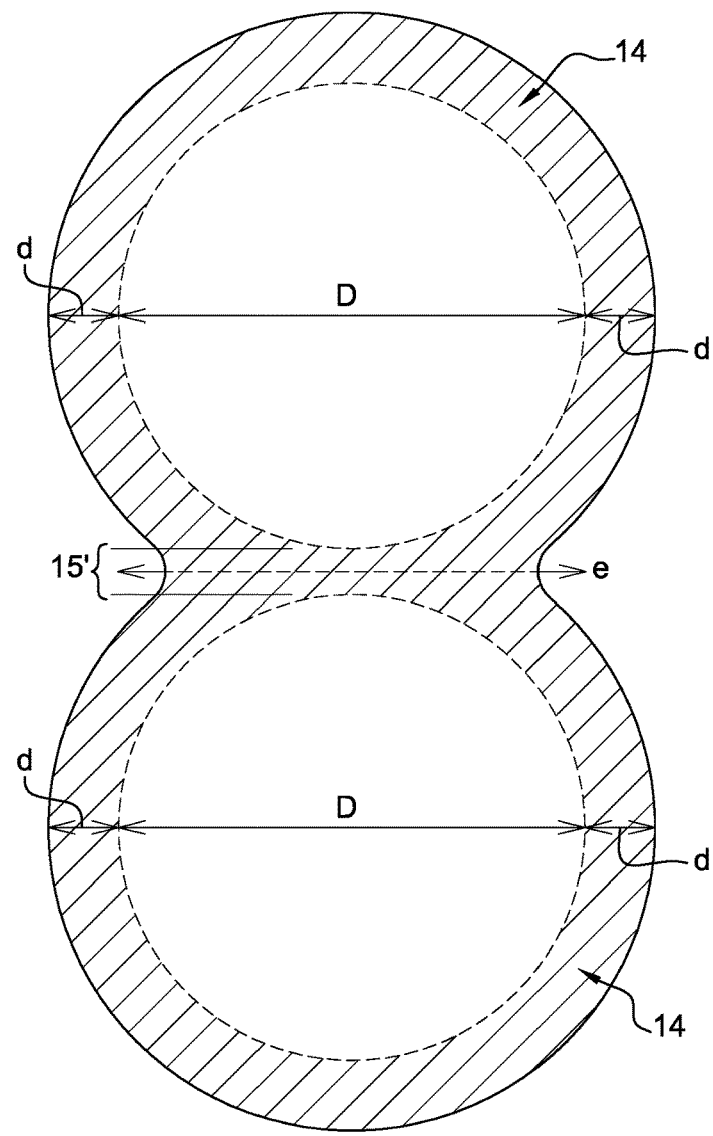
FIG. 1e is a top view of a packaging article in an unfolded state, according to various embodiments of the present disclosure.

As a variant, the second lap may be formed by the first lap folded on itself 11' shown in FIG. 1d) in cross section and FIG. 1e) in top view. The lap is folded on itself along the folding axis e which defines a cavity in which is found the dye composition comprising at least one direct dye 18' and optionally at least one chemical oxidizing agent as defined below and/or at least one other dye different from the powdered direct dyes and/or the excipients as defined below, which are preferably in powder form 19', optionally separated by one or more water-soluble laps 16'. The lap 11', once filled with the ingredients 19' and with the water-soluble lap(s) 16', is folded along the axis e, forming a folding zone 15' and then joined at a peripheral region 14, the shaded part of Figure e), preferably via any suitable fixing means such as glueing, welding, especially heat-welding, and in particular by entanglement. The thickness of the water-soluble lap 11' and the transverse dimensions satisfy the same criteria as those defined for the lap 11 or 12 of FIG. 1b).

The fibres forming the first lap 11 or 11' and the second lap 12, and the additional laps 16, 16' and 17, are preferably water-soluble, i.e. they consist of water-soluble fibres. These fibres are, for example, nonwoven water-soluble fibres such as PVA fibres, polysaccharide fibres such as glucomannans or starches, or any other polymer or compound that is capable of forming water-soluble fibres or yarns, obtained, for example, by extrusion.

The laps 11, 11' and 12 and the optional additional laps 16, 16' and 17, which are preferably made of nonwoven, generally have a basis weight of less than or equal to 60 g/m$^2$, or even less than or equal to 50 g/m$^2$ and better still less than or equal to 45 g/m$^2$. In a variant, the basis weight of at least one layer may be greater than 60 g/m$^2$.

The packaging articles comprising water-soluble fibres according to the invention are preferably soluble in water or in an aqueous composition with a dissolution time of the packaging article preferably of not more than one hour.

Process for Preparing the Packaging Article:

The envelope i) delimits or defines a cavity that is filled with an anhydrous dye composition ii) comprising at least one direct dye, preferably in powder or paste form, and optionally at least one anhydrous chemical oxidizing agent iii), preferably in powder or paste form, the article is then closed by folding the envelope i) on itself with its contents, followed by assembly at its periphery, for example by glueing or welding, preferably by heat-welding, or alternatively, if the article contains an envelope consisting of two laps, the anhydrous dye composition ii) preferably in powder or paste form and optionally at least one anhydrous chemical oxidizing agent preferably in powder or paste form iii) are placed on the first lap, the article is closed by means of a second lap which covers the ingredients ii) and iii) placed on the first lap and which is assembled, for example, by glueing or welding at its periphery, preferably by heat-welding at its periphery, so as to obtain a hermetic article, which does not allow the powders or pastes contained in the said article to pass into the atmosphere. When the envelope and the laps comprise several water-soluble laps of nonwovens, these nonwovens may be assembled especially by heat-welding at their periphery. Preferably, the heat-welding is performed with entanglement of the fibres of the parts of the envelope to be welded.

ii) At Least One Direct Dye

As has been indicated previously, the anhydrous dye composition comprises at least one direct dye which may be in powder or paste form, preferably in powder form.

The term "direct dye" means natural and/or synthetic dyes. These are dyes that will spread superficially on the fibre. The direct dyes may be onionic, nonionic or cationic. They are preferably cationic or nonionic, either as a mixture or as individual dyes.

Mention may be made, as direct dye according to the invention, of the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, in particular nitro(hetero)aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines; thioindigos; thiopyronines; triarylmethanes or xanthenes.

More particularly, the direct dyes of the invention are chosen from neutral, acidic or cationic nitrobenzene direct dyes, neutral, acidic or cationic azo direct dyes, tetraazapentamethine dyes, neutral, acidic or cationic quinone and in particular anthraquinone dyes, azine direct dyes, triarylmethane direct dyes, azomethine direct dyes and natural direct dyes.

According to one embodiment, the direct dyes of the invention are anionic. These anionic direct dyes are dyes commonly known as "acid dyes" for their affinity with alkaline substances (see, for example, "*Industrial Dyes, Chemistry, Properties, Application*", Klaus Hunger Ed. Wiley-VCH Verlag GmbH & Co. KGaA, Weinheim 2003). Anionic or acid dyes are known in the literature (see, for example, "*Ullman's Encyclopedia of Industrial Chemistry*", Azo Dyes, 2005 Wiley-VCH Verlag GmbH & Co. KGaA, Weinheim 10.1002/14356007.a03 245, point 3.2; ibid, Textile Auxiliaries, 2002 Wiley-VCH Verlag GmbH & Co. KGaA, Weinheim 10.1002/14356007.a26 227 and "*Ashford's Dictionary of Industrial Chemicals*", Second Edition, p. 14-p. 39, 2001).

The term "anionic direct dye" means any direct dye comprising in its structure at least one sulfonate $SO_3^-$ group and/or at least one carboxylate group $C(O)O^-$ and optionally one or more anionic groups $G^-$ with $G^-$, which may be identical or different, representing an anionic group chosen from alkoxide $O^-$, thiolate $S^-$, carboxylate and thiocarboxylate: $C(Q)Q'^-$, with Q and Q', which may be identical or different, representing an oxygen or sulfur atom; preferably, $G^-$ represents a carboxylate, i.e. Q and Q' represent an oxygen atom.

The preferred anionic dyes are chosen from acidic nitro direct dyes, acidic azo dyes, acidic azine dyes, acidic triarylmethane dyes, acidic indoamine dyes, acidic anthraquinone dyes, indigoid dyes and acidic natural dyes, each of these dyes containing at least one sulfonate or carboxylate group.

As anionic dyes according to the invention, mention may be made of the dyes of formulae (II), (II'), (III), (III'), (IV), (IV'), (V), (V'), (VI), (VII), (VIII) and (IX) below:

a) the diaryl anionic azo dyes of formula (II) or (II'):

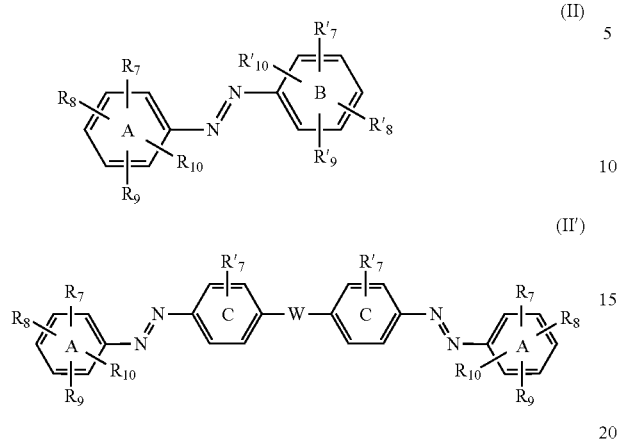

in which formulae (II) and (II'):

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;

nitro, $R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a cationic counterion such as an alkali metal (Na, K) or an alkaline-earth metal (Ca);

$(O)CO^-$—, $M^+$ with $M^+$ as defined previously;

R"—$S(O)_2$—, with R" representing a hydrogen atom or an alkyl, aryl, (di)(alkyl)amino or aryl(alkyl)amino group; preferentially a phenylamino or phenyl group;

R'''—$S(O)_2$—X'— with R''' representing an alkyl or optionally substituted aryl group, X' as defined previously;

(di)(alkyl)amino;

aryl(alkyl)amino optionally substituted with one or more groups chosen from i) nitro; ii) nitroso; iii) $(O)_2S(O^-)$—, $M^+$ and iv) alkoxy with $M^+$ as defined previously;

optionally substituted heteroaryl; preferentially a benzothiazolyl group;

cycloalkyl; especially cyclohexyl,

Ar—N=N— with Ar representing an optionally substituted aryl group; preferentially a phenyl optionally substituted with one or more alkyl, $(O)_2S(O^-)$—, $M^+$ or phenylamino groups;

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N=N— and xi) optionally substituted aryl(alkyl)amino; with $M^+$, $R^o$, X, X', X" and Ar as defined previously;

W represents a sigma bond σ, an oxygen or sulfur atom, or a divalent radical i) —NR— with R as defined previously, or ii) methylene —$C(R_a)(R_b)$— with $R_a$ and $R_b$, which may be identical or different, representing a hydrogen atom or an aryl group, or alternatively $R_a$ and $R_b$ form, with the carbon atom that bears them, a spiro cycloalkyl; preferentially, W represents a sulfur atom or $R_a$ and $R_b$ together form a cyclohexyl;

it being understood that formulae (II) and (II') comprise at least one sulfonate $(O)_2S(O^-)$—, $M^+$ or carboxylate $(O)C(O^-)$—, $M^+$ radical on one of the rings A, A', B, B' or C with $M^+$ as defined previously;

as examples of dyes of formula (II), mention may be made of Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1 and Food Black 2;

and as examples of dyes of formula (II'), mention may be made of Acid Red 111, Acid Red 134 and Acid yellow 38;

b) the pyrazolone anionic azo dyes of formulae (III) and (III'):

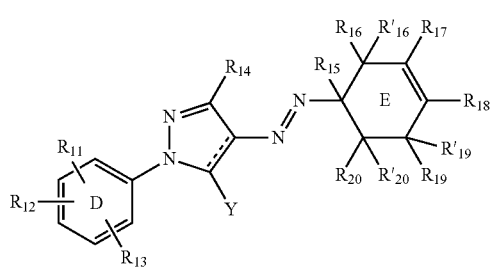

(III')

[Chemical structure of formula (III')]

in which formulae (III) and (III'):
- $R_{11}$, $R_{12}$ and $R_{13}$, which may be identical or different, represent a hydrogen or halogen atom, an alkyl group or —(O)$_2$S(O$^-$), M$^+$ with M$^+$ as defined previously;
- $R_{14}$ represents a hydrogen atom, an alkyl group or a group —C(O)O$^-$, M$^+$ with M$^+$ as defined previously;
- $R_{15}$ represents a hydrogen atom;
- $R_{16}$ represents an oxo group, in which case R'$_{16}$ is absent, or alternatively $R_{15}$ with $R_{16}$ together form a double bond;
- $R_{17}$ and $R_{18}$, which may be identical or different, represent a hydrogen atom or a group chosen from:
  - (O)$_2$S(O$^-$)—, M$^+$ with M$^+$ as defined previously;
  - Ar—O—S(O)$_2$— with Ar representing an optionally substituted aryl group; preferentially a phenyl optionally substituted with one or more alkyl groups;
- $R_{19}$ and $R_{20}$ together form either a double bond, or a benzo group D', which is optionally substituted;
- R'$_{16}$, R'$_{19}$ and R'$_{20}$, which may be identical or different, represent a hydrogen atom or an alkyl or hydroxyl group;
- $R_{21}$ represents a hydrogen atom or an alkyl or alkoxy group;
- $R_a$ and $R_b$, which may be identical or different, are as defined previously, preferentially $R_a$ represents a hydrogen atom and $R_b$ represents an aryl group;
- Y represents either a hydroxyl group or an oxo group;
- ---- represents a single bond when Y is an oxo group; and represents a double bond when Y represents a hydroxyl group;
- it being understood that formulae (III) and (III') comprise at least one sulfonate group (O)$_2$S(O$^-$)—, M$^+$ on one of the rings D or E or formulae (III) and (III') comprise at least one carboxylate group (O)C(O$^-$)—, M$^+$ with M$^+$ as defined previously;
- as examples of dyes of formula (III), mention may be made of Acid Red 195, Acid Yellow 23, Acid Yellow 27, Acid Yellow 76, and, as examples of dyes of formula (III'), mention may be made of the ammonium salt derived from Acid Yellow 17;

c) the anthraquinone dyes of formulae (IV) and (IV'):

(IV)

[Chemical structure of formula (IV)]

(IV')

[Chemical structure of formula (IV')]

in which formulae (IV) and (IV'):
- $R_{22}$, $R_{23}$, $R_{24}$, $R_{25}$, $R_{26}$ and $R_{27}$, which may be identical or different, represent a hydrogen or halogen atom or a group chosen from:
  - alkyl;
  - hydroxyl, mercapto;
  - alkoxy, alkylthio;
  - optionally substituted aryloxy or arylthio, preferentially substituted with one or more groups chosen from alkyl and (O)$_2$S(O$^-$)—, M$^+$ with M$^+$ as defined previously;
  - aryl(alkyl)amino optionally substituted with one or more groups chosen from alkyl and (O)$_2$S(O$^-$)—, M$^+$ with M$^+$ as defined previously;
  - (di)(alkyl)amino;
  - (di)(hydroxyalkyl)amino;
  - (O)$_2$S(O$^-$)—, M$^+$ with M$^+$ as defined previously;
- Z' represents a hydrogen atom or a group NR$_{28}$R$_{29}$ with $R_{28}$ and $R_{29}$, which may be identical or different, representing a hydrogen atom or a group chosen from:
  - alkyl;
  - polyhydroxyalkyl such as hydroxyethyl;
  - aryl optionally substituted with one or more groups, particularly i) alkyl such as methyl, n-dodecyl, n-butyl; ii) (O)$_2$S(O$^-$)—, M$^+$ with M$^+$ as defined previously; iii) R°—C(X)—X'—, R°—X'—C(X)—, R°—X'—C(X)—X"— with R°, X, X' and X" as defined previously, preferentially R° represents an alkyl group;
  - cycloalkyl; especially cyclohexyl;
- Z represents a group chosen from hydroxyl and NR'$_{28}$R'$_{29}$ with R'$_{28}$ and R'$_{29}$, which may be identical or different, representing the same atoms or groups as $R_{28}$ and $R_{29}$ as defined previously;

it being understood that formulae (IV) and (IV') comprise at least one sulfonate group $(O)_2S(O^-)$—, $M^+$ with $M^+$ as defined previously;

as examples of dyes of formula (IV), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43 and Mordant Red 3; and as examples of dyes of formula (IV'), mention may be made of the ammonium salt derived from Acid Black 48;

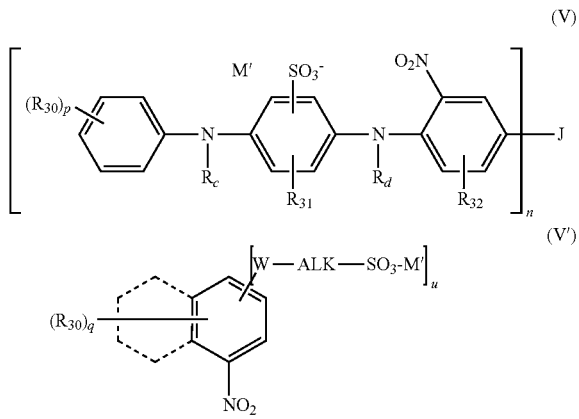

in which formulae (V) and (V'):
- $R_{30}$, $R_{31}$ and $R_{32}$, which may be identical or different, represent a hydrogen or halogen atom, or a group chosen from:
  - alkyl;
  - alkoxy optionally substituted with one or more hydroxyl groups, alkylthio optionally substituted with one or more hydroxyl groups;
  - hydroxyl, mercapto;
  - nitro, nitroso;
  - (poly)haloalkyl;
  - $R^o$—C(X)—X'—, $R^o$—X'—C(X)—, $R^o$—X'—C(X)—X"— with $R^o$; X, X' and X" as defined previously;
  - $(O)_2S(O^-)$—, $M^+$ with $M^+$ as defined previously;
  - $(O)CO^-$—, $M^+$ with $M^+$ as defined previously;
  - (di)(alkyl)amino;
  - (di)(hydroxyalkyl)amino;
  - heterocycloalkyl such as piperidino, piperazino or morpholino;
- in particular, $R_{30}$, $R_{31}$ and $R_{32}$ represent a hydrogen atom;
- $R_c$ and $R_d$, which may be identical or different, represent a hydrogen atom or an alkyl group;
- W is as defined previously; W particularly represents a group —NH—;
- ALK represents a linear or branched divalent $C_1$-$C_6$ alkylene group; in particular, ALK represents a group —$CH_2$—$CH_2$—;
- n is 1 or 2;
- p represents an integer between 1 and 5 inclusively;
- q represents an integer between 1 and 4 inclusively;
- u is 0 or 1;
- when n is 1, J represents a nitro or nitroso group; particularly nitro;
- when n is 2, J represents an oxygen or sulfur atom, or a divalent radical —$S(O)_m$— with m representing an integer 1 or 2; preferentially J represents a radical —$SO_2$—;
- M' is as defined previously for $M^+$;

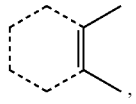

which may be present or absent, represents a benzo group optionally substituted with one or more groups $R_{30}$ as defined previously;

it being understood that formulae (V) and (V') comprise at least one sulfonate group $(O)_2S(O^-)$—, $M^+$ or carboxylate group $(O)C(O^-)$—, $M^+$ with $M^+$ as defined previously;

as examples of dyes of formula (V), mention may be made of: Acid Brown 13 and Acid Orange 3; as examples of dyes of formula (V'), mention may be made of: Acid Yellow 1, sodium salt of 2,4-dinitro-1-naphthol-7-sulfonic acid, 2-piperidino-5-nitrobenzenesulfonic acid, 2-(4'-N,N(2"-hydroxyethyl)amino-2'-nitro)anilineethanesulfonic acid and 4-β-hydroxyethylamino-3-nitrobenzenesulfonic acid;

d) the triarylmethane dyes of formula (VI):

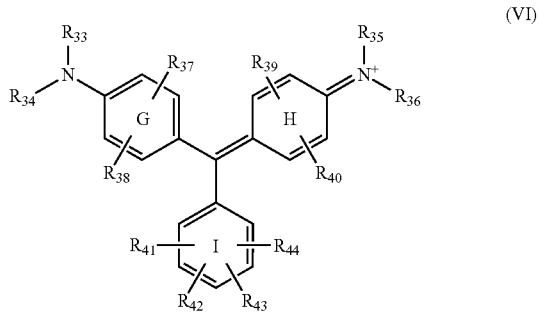

in which formula (VI):
- $R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl group and benzyl optionally substituted with a group $(O)_mS(O^-)$—, $M^+$ with $M^+$ and m as defined previously;
- $R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:
  - alkyl;
  - alkoxy, alkylthio;
  - (di)(alkyl)amino;
  - hydroxyl, mercapto;
  - nitro, nitroso;
  - $R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;
  - $(O)_2S(O^-)$—, $M^+$ with $M^+$ representing a hydrogen atom or a cationic counterion;
  - $(O)CO^-$—, $M^+$ with $M^+$ as defined previously;
- or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi)

(di)(alkyl)amino; vii) R°—C(X)—X'—; viii) R°—X'—C(X)— and ix) R°—X'—C(X)—X"—; with M+, R°, X, X' and X" as defined previously;

particularly, $R_{37}$ to $R_{40}$ represent a hydrogen atom, and $R_{41}$ to $R_{44}$, which may be identical or different, represent a hydroxyl group or $(O)_2S(O^-)$—, M+; and when $R_{43}$ with $R_{44}$ together form a benzo group, it is preferentially substituted with a group $(O)_2S(O^-)$—;

it being understood that at least one of the rings G, H, I or I' comprises at least one sulfonate $(O)_2S(O^-)$—, M+ or carboxylate $(O)C(O^-)$—, M+ group as defined previously;

as examples of dyes of formula (VI), mention may be made of: Acid Blue 1; Acid Blue 3; Acid Blue 7, Acid Blue 9; Acid Violet 49 and Acid Green 50;

e) the xanthene-based dyes of formula (VII):

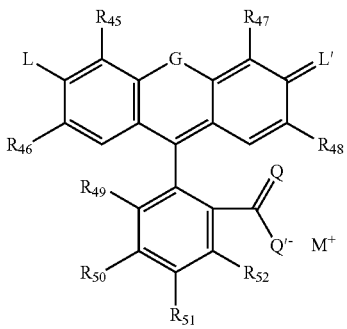

(VII)

in which formula (VII):

$R_{45}$, $R_{46}$, $R_{47}$ and $R_{48}$, which may be identical or different, represent a hydrogen or halogen atom;

$R_{49}$, $R_{50}$, $R_{51}$ and $R_{52}$, which may be identical or different, represent a hydrogen or halogen atom, or a group chosen from:
alkyl;
alkoxy, alkylthio;
hydroxyl, mercapto;
nitro, nitroso;
$(O)_2S(O^-)$—, M+ with M+ representing a hydrogen atom or a cationic counterion;
$(O)CO^-$—, M+ with M+ as defined previously;
particularly $R_{53}$, $R_{54}$, $R_{55}$ and $R_{48}$ represent a hydrogen or halogen atom;

G represents an oxygen or sulfur atom or a group $NR_e$ with $R_e$ as defined previously; particularly G represents an oxygen atom;

L represents an alkoxide $O^-$, M+; a thioalkoxide $S^-$, M+ or a group $NR_f$, with $R_f$ representing a hydrogen atom or an alkyl group and M+ as defined previously; M+ is particularly sodium;

L' represents an oxygen or sulfur atom or an ammonium group: $N^+R_fR_g$, with $R_f$ and $R_g$, which may be identical or different, representing a hydrogen atom, an alkyl group or optionally substituted aryl; L' represents particularly an oxygen atom or a phenylamino group optionally substituted with one or more alkyl or $(O)_mS(O^-)$—, M+ groups with m and M+ as defined previously;

Q and Q', which may be identical or different, represent an oxygen or sulfur atom; particularly Q and Q' represent an oxygen atom;

M+ is as defined previously;

it being understood that formula (VII) comprises at least one sulfonate group $(O)_2S(O^-)$—, M+ or carboxylate group $(O)C(O^-)$—, M+ with M+ as defined previously;

as examples of dyes of formula (VII), mention may be made of: Acid Yellow 73; Acid Red 51; Acid Red 87; Acid Red 92; Acid Red 95 and Acid Violet 9;

f) the indole-based dyes of formula (VIII):

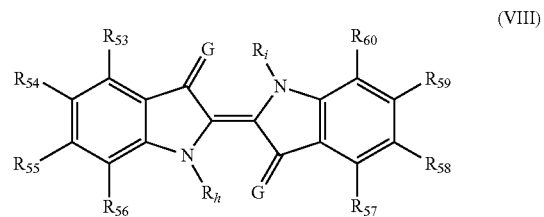

(VIII)

$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:
alkyl;
alkoxy, alkylthio;
hydroxyl, mercapto;
nitro, nitroso;
R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, M+ with M+ as defined previously;
$(O)CO^-$—, M+ with M+ as defined previously;

G represents an oxygen or sulfur atom or a group $NR_e$ with $R_e$ as defined previously; particularly G represents an oxygen atom;

$R_i$ and $R_h$, which may be identical or different, represent a hydrogen atom or an alkyl group;

it being understood that formula (VIII) comprises at least one sulfonate group $(O)_2S(O^-)$—, M+ or carboxylate group $(O)C(O^-)$—, M+ with M+ as defined previously;

as examples of dyes of formula (VIII), mention may be made of the ammonium salt derived from: Acid Blue 74;

g) the quinoline-based dyes of formula (IX):

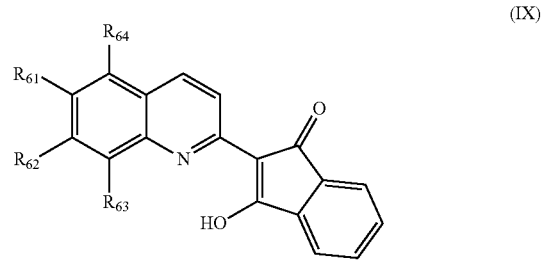

(IX)

$R_{61}$ represents a hydrogen or halogen atom or an alkyl group;

$R_{62}$, $R_{63}$ and $R_{64}$, which may be identical or different, represent a hydrogen atom or a group $(O)_2S(O^-)$—, M+ with M+ as defined previously;

or alternatively $R_{61}$ with $R_{62}$, or $R_{61}$ with $R_{64}$, together form a benzo group optionally substituted with one or more groups $(O)_2S(O^-)$—, M+ with M+ representing a hydrogen atom or a cationic counterion;

it being understood that formula (IX) comprises at least one sulfonate group (O)$_2$S(O$^-$)—, with M$^+$ as defined previously;

as examples of dyes of formula (IX), mention may be made of: Acid Yellow 2, Acid Yellow 3 and Acid Yellow 5. More particularly, the anionic direct dyes that are useful in the invention may be chosen from the following dyes:

| | |
|---|---|
| (C.I. 45380) | Acid Red 87 belonging to formula (VII) |
| (C.I. 10316) | salts of 2,4-dinitro-1-naphthol-7-sulfonic acid belonging to formula (V') |
| (C.I. 10383) | Acid Orange 3 belonging to formula (V) |
| (C.I. 13015) | Acid Yellow 9/Food Yellow 2 belonging to formula (II) |
| (C.I. 14780) | /Direct Red 45/Food Red 13 belonging to formula (II) |
| (C.I. 13711) | Acid Black 52 belonging to formula (II) |
| (C.I. 13065) | Acid Yellow 36 belonging to formula (II) |
| (C.I. 14700) | salt of 1-hydroxy-2-(2',4'-xylyl-5-sulfonatoazo)naphthalene-4-sulfonic acid/Food Red 1 belonging to formula (II) |
| (C.I. 14720) | Acid Red 14/Food Red 3/Mordant Blue 79 belonging to formula (II) |
| (C.I. 14805) | salt of 4-hydroxy-3-[(2-methoxy-5-nitrophenyl)diaza]-6-(phenylamino)naphthalene-2-sulfonic acid/Acid Brown 4 belonging to formula (II) |
| (C.I. 15510) | Acid Orange 7/Pigment Orange 17/Solvent Orange 49 belonging to formula (II) |
| (C.I. 15985) | Food Yellow 3/Pigment Yellow 104 belonging to formula (II) |
| (C.I. 16185) | Acid Red 27/Food Red 9 belonging to formula (II) |
| (C.I. 16230) | Acid Orange 10/Food Orange 4 belonging to formula (II) |
| (C.I. 16250) | Acid Red 44 belonging to formula (II) |
| (C.I. 17200) | Acid Red 33/Food Red 12 belonging to formula (II) |
| (C.I. 15685) | Acid Red 184 belonging to formula (II) |
| (C.I. 19125) | Acid Violet 3 belonging to formula (II) |
| (C.I. 18055) | salt of 1-hydroxy-2-(4'-acetamidophenylazo)-8-acetamidonaphthalene-3,6-disulfonic acid/Acid Violet 7/Food Red 11 belonging to formula (II) |
| (C.I. 18130) | Acid Red 135 belonging to formula (II) |
| (C.I. 19130) | Acid Yellow 27 belonging to formula (III) |
| (C.I. 19140) | Acid Yellow 23/Food Yellow 4 belonging to formula (III) |
| (C.I. 20170) | 4'-(sulfonato-2'',4''-dimethyl)bis(2,6-phenylazo)-1,3-dihydroxybenzene/Acid Orange 24 belonging to formula (II) |
| (C.I. 20470) | salt of 1-amino-2-(4'-nitrophenylazo)-7-phenylazo-8-hydroxynaphthalene-3,6-disulfonic acid/Acid Black 1 (II) |
| (C.I. 23266) | (4-((4-methylphenyl)sulfonyloxy)phenylazo)-2,2'-dimethyl-4-((2-hydroxy-5,8-disulfonato)naphthylazo)biphenyl/Acid Red 111 belonging to formula (II') |
| (C.I. 27755) | Food Black 2 belonging to formula (II) |
| (C.I. 25440) | 1-(4'-sulfonatophenylazo)-4-((2''-hydroxy-3''-acetylamino-6'',8''-disulfonato)naphthylazo)-6-sulfonatonaphthalene (tetrasodium salt)/Food Black 1 belonging to formula (II) |
| (C.I. 42090) | Acid Blue 9 belonging to formula (VI) |
| (C.I. 60730) | Acid Violet 43 belonging to formula (IV) |
| (C.I. 61570. | Acid Green 25 belonging to formula (IV) |
| (C.I. 62045) | salt of 1-amino-4-cyclohexylamino-9,10-anthraquinone-2-sulfonic acid/Acid Blue 62 belonging to formula (IV) |
| (C.I. 62105) | Acid Blue 78 belonging to formula (IV) |
| (C.I. 14710) | salt of 4-hydroxy-3-((2-methoxyphenyl)azo)-1-naphthalenesulfonic acid/Acid Red 4 belonging to formula (II) |
| | 2-piperidino-5-nitrobenzenesulfonic acid belonging to formula (V') |
| | 2-(4''-N,N-(2''-hydroxyethyl)amino-2'-nitro)anilineethanesulfonic acid belonging to formula (V') |
| | 4-β-hydroxyethylamino-3-nitrobenzene sulfonic acid belonging to formula (V') |
| (C.I. 42640) | Acid Violet 49 belonging to formula (VI) |
| (C.I. 42080) | Acid Blue 7 belonging to formula (VI) |
| (C.I. 58005) | ammonium salts of 1,2-dihydroxy-3-sulfoanthraquinone/Mordant Red 3 belonging to formula (IV) |
| (C.I. 62055. | salt of 1-amino-9,10-dihydro-9,10-dioxo-4-(phenylamino)-2-anthracenesulfonic acid/Acid Blue 25 belonging to formula (IV) |
| (C.I. 14710. | salt of 4-hydroxy-3-((2-methoxyphenyl)azo)-1-naphthalenesulfonic acid/Acid Red 4 belonging to formula (II) |

Most of these dyes are described in particular in the Colour Index published by The Society of Dyers and Colourists, P.O. Box 244, Perkin House, 82 Grattan Road, Bradford, Yorkshire, BD1 2JBN England.

The anionic dyes that are most particularly preferred are the dyes designated in the Colour Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl[3-sulfophenyl)methyl]amino]phenyl](2-sulfophenyl)methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]benzenesulfonic acid). It is also possible to use compounds corresponding to the mesomeric or tautomeric forms of structures (II) to (IX).

More preferentially, the anionic dyes of formula (I) according to the invention are chosen from those of formulae (II), (III) and (IV).

According to a particular embodiment of the invention, the direct dyes of the invention are chosen from (IIa), (IIIa) and (IVa) below:

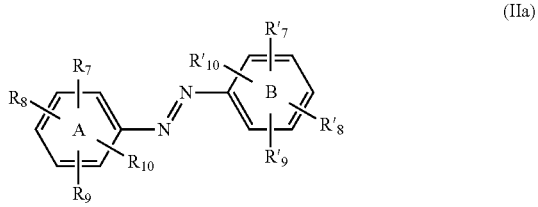
(IIa)

in which formula (IIa):

$R_7$, $R_8$, $R_9$, $R_{10}$, $R'_7$, $R'_8$, $R'_9$ and $R'_{10}$, which may be identical or different, represent a hydrogen atom or a group chosen from:
hydroxyl,
nitro, nitroso;
(di)(alkyl)amino;
$(O)_2S(O^-)$—, $M^+$ with $M^+$ representing a hydrogen atom or a cationic counterion as defined previously; and
Ar—N═N— with Ar representing an optionally substituted aryl group; preferentially a phenyl optionally substituted with one or more alkyl or $(O)_2S(O^-)$—, $M^+$ groups;
or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from a) $(O)_2S(O^-)$—, $M^+$; b) hydroxyl; c) Ar—N═N—; with $M^+$ and Ar as defined previously;

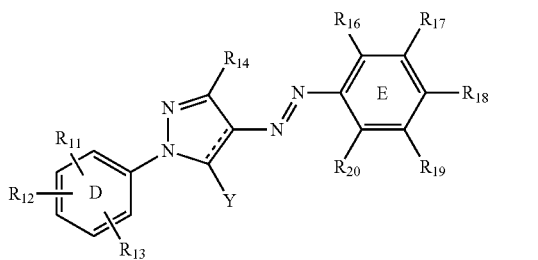
(IIIa)

in which formula (IIIa):

$R_{11}$, $R_{12}$ and $R_{13}$, which may be identical or different, represent a hydrogen or halogen atom, an alkyl group or —$(O)_2S(O^-)$, $M^+$ with $M^+$ as defined previously;

$R_{14}$ represents a hydrogen atom, an alkyl group or a group —C(O)O$^-$, $M^+$ with $M^+$ as defined previously;

$R_{16}$, $R_{17}$, $R_{18}$, $R_{19}$ and $R_{20}$, which may be identical or different, represent a hydrogen atom, an alkyl or hydroxyl group or $(O)_2S(O^-)$—, $M^+$ with $M^+$ as defined previously;

Y represents either a hydroxyl group or an oxo group;

- - - - represents a single bond when Y is an oxo group; and represents a double bond when Y represents a hydroxyl group;

it being understood that formula (IIIa) comprises at least one sulfonate group $(O)_2S(O^-)$—, $M^+$ on one of the rings D or E or carboxylate $(O)C(O^-)$—, $M^+$;

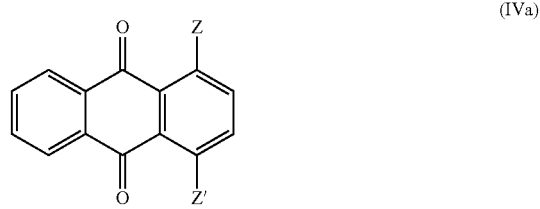
(IVa)

in which formula (IVa):

Z' represents a group $NR_{28}R_{29}$ with $R_{28}$ representing a hydrogen atom or an alkyl group and $R_{29}$ representing an aryl group optionally substituted particularly with one or more groups chosen from i) alkyl such as methyl and ii) $(O)_2S(O^-)$—, $M^+$ with $M^+$ as defined previously;

Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously;

it being understood that formula (IVa) comprises at least one sulfonate group $(O)_2S(O^-)$—, $M^+$;

examples that may be mentioned include the following anionic dyes:

| Commercial name | Corresponding structure |
|---|---|
| Acid Orange 7 | (belonging to formulae (II) and (IIa)) |

| Commercial name | Corresponding structure |
|---|---|
| Acid Black 1 | 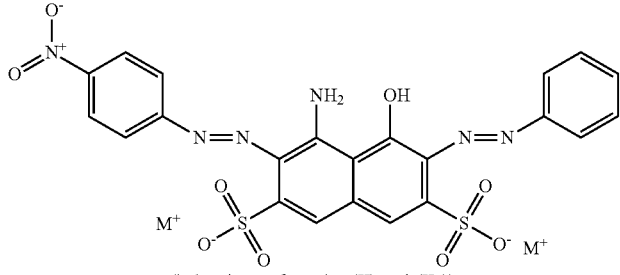<br>(belonging to formulae (II) and (IIa)) |
| Acid Red 18 | 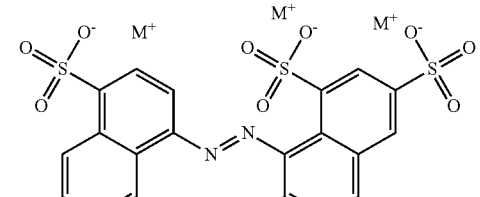<br>(belonging to formulae (II) and (IIa)) |
| Acid Yellow 23 | 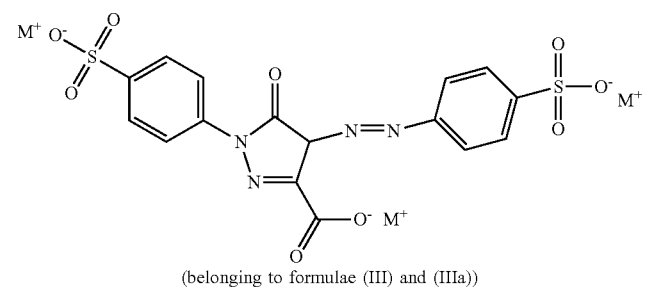<br>(belonging to formulae (III) and (IIIa)) |
| Acid Violet 43 | 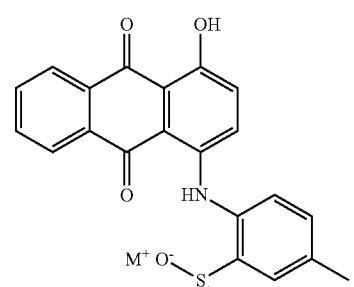<br>(belonging to formulae (IV) and (IVa)) | with $M^+$, which may be identical or different, being a cationic counterion as defined previously.

According to a particular embodiment of the invention, the direct dyes are benzene-based dyes that are usually neutral. More preferentially, the benzene-based direct dyes of the invention are chosen from the compounds of formula (X) below:

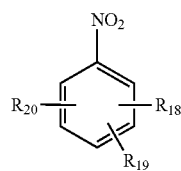

(X)

in which formula (X):
- $R_{18}$ represents an amino radical; an amino radical monosubstituted or disubstituted with a $C_1$-$C_4$ alkyl, $C_1$-$C_4$ monohydroxyalkyl, $C_2$-$C_4$ polyhydroxyalkyl, $C_1$-$C_4$ aminoalkyl, mono($C_1$-$C_4$)alkylamino($C_1$-$C_4$)alkyl, di($C_1$-$C_4$)alkylamino($C_1$-$C_4$)alkyl, $C_1$-$C_4$ ureidoalkyl, aryl, aryl in which the aryl ring is substituted with one or more hydroxyl, carboxyl, amino or di($C_1$-$C_4$)alkylamino radicals,
- $R_{19}$ represents a hydrogen atom; an amino radical; hydroxyl; $C_1$-$C_4$ alkyl; $C_1$-$C_4$ alkoxy; $C_1$-$C_4$ monohydroxyalkyl; $C_2$-$C_4$ polyhydroxyalkyl; $C_1$-$C_4$ monohydroxyalkoxy; $C_2$-$C_4$ polyhydroxyalkoxy; $C_1$-$C_4$ aminoalkoxy; an amino radical monosubstituted or disubstituted with a $C_1$-$C_4$ alkyl radical, $C_1$-$C_4$ monohydroxyalkyl, $C_2$-$C_4$ polyhydroxyalkyl, $C_1$-$C_4$ aminoalkyl, mono($C_1$-$C_4$)alkylamino($C_1$-$C_4$)alkyl, di($C_1$-$C_4$)alkylamino($C_1$-$C_4$)alkyl, $C_1$-$C_4$ ureidoalkyl, aryl, aryl in which the aryl ring is substituted with one or more hydroxyl, carboxyl, amino or di($C_1$-$C_4$)alkylamino radicals;
- $R_{20}$ represents a hydrogen or halogen atom, a $C_1$-$C_4$ alkyl radical or a nitro group.

Among the nitrobenzene dyes of formula (X) above, mention may be made most particularly of: 2-amino-4-methyl-5-N-(β-hydroxyethyl)aminonitrobenzene; 4-N-(β-ureidoethyl)aminonitrobenzene; 4-(N-ethyl-N-β-hydroxyethyl)amino-1-N-(β-hydroxyethyl)aminonitrobenzene; 2-N-(β-hydroxyethyl)amino-5-methylnitrobenzene; 5-chloro-3-N-(ethyl)amino-4-hydroxynitrobenzene; 5-amino-3-chloro-4-hydroxynitrobenzene; 2-N-(γ-hydroxypropyl)amino-5-N,N-bis(β-hydroxyethyl)aminonitrobenzene; 5-hydroxy-2-N-(γ-hydroxypropyl)aminonitrobenzene; 1,3-bis(β-hydroxyethyl)amino-4-chloro-6-nitrobenzene; 2,4-diaminonitrobenzene; 3,4-diaminonitrobenzene; 2,5-diaminonitrobenzene; 3-amino-4-hydroxynitrobenzene; 4-amino-3-hydroxynitrobenzene; 5-amino-2-hydroxynitrobenzene; 2-amino-5-hydroxynitrobenzene; 4-amino-3-hydroxynitrobenzene; 5-amino-2-hydroxynitrobenzene; 2-amino-3-hydroxynitrobenzene; 2-amino-5-N-(β-hydroxyethyl)aminonitrobenzene; 2-amino-5-N,N-bis(β-hydroxyethyl)aminonitrobenzene; 2,5-N,N'-(β-hydroxyethyl)aminonitrobenzene; 2-N-(β-hydroxyethyl)amino-5-N,N-bis(β-hydroxyethyl)aminonitrobenzene; 2-amino-5-N-(methyl)aminonitrobenzene; 2-N-(methyl)amino-5-N,N-bis(β-hydroxyethyl)aminonitrobenzene; 2-N-(methyl)amino-5-(N-methyl-N-β-hydroxyethyl)aminonitrobenzene; 2,5-N,N'-(β-hydroxyethyl)aminonitrobenzene; 2-N-(β-hydroxyethyl)amino-5-hydroxynitrobenzene; 3-methoxy-4-N-(β-hydroxyethyl)aminonitrobenzene; 2-N-(methyl)amino-4-β-hydroxyethyloxynitrobenzene; 2-amino-3-methylnitrobenzene; 2-N-(β-hydroxyethyl)amino-5-aminonitrobenzene; 2-amino-4-chloro-5-N-(β-hydroxyethyl)aminonitrobenzene; 2-amino-4-methyl-5-N-(β-hydroxyethyl)aminonitrobenzene; 2-amino-4-methyl-5-N-(methyl)aminonitrobenzene; 2-N-(β-hydroxyethyl)amino-5-methoxynitrobenzene; 2-amino-5-β-hydroxyethyloxynitrobenzene; 2-N-(β-hydroxyethyl)aminonitrobenzene; 3-amino-4-N-(β-hydroxyethyl)aminonitrobenzene; 3-β-hydroxyethyloxy-4-N-(β-hydroxyethyl)aminonitrobenzene; 2-N-(methyl)amino-4-β,γ-dihydroxypropyloxynitrobenzene; 2-N-(β-hydroxyethyl)amino-5-β-hydroxyethyloxynitrobenzene; 2-N-(β-hydroxyethyl)amino-5-β,γ-dihydroxypropyloxynitrobenzene; 2-hydroxy-4-N-(β-hydroxyethyl)aminonitrobenzene; 2-N-(methyl)amino-4-methyl-5-aminonitrobenzene; 2-amino-4-isopropyl-5-N-(methyl)aminonitrobenzene; 2-N-(methyl)amino-5-(N-methyl-N-β,γ-dihydroxypropyl)aminonitrobenzene; 3-N-(β-hydroxyethyl)amino-4-N-(β-hydroxyethyl)aminonitrobenzene; 2-amino-4-methyl-5-N-(β,γ-dihydroxypropyl)aminonitrobenzene; 2-amino-4-methyl-5-hydroxynitrobenzene; 2-N-(β-hydroxyethyl)amino-4-N-(β-hydroxyethyl)aminonitrobenzene; 2-amino-5-N-(β-aminoethyl)aminonitrobenzene; 2-N-(β-aminoethyl)amino-5-methoxynitrobenzene; 2-N-(methyl)amino-5-N-(β-aminoethyl)aminonitrobenzene; 2-N-(β-aminoethyl)amino-4-N,N-(dimethyl)aminonitrobenzene; 3-amino-4-N-(β-aminoethyl)aminonitrobenzene; 2-amino-4-methyl-5-N-(β-aminoethyl)aminonitrobenzene; 2-N-(β-aminoethyl)amino-5-N,N-bis(β-hydroxyethyl)aminonitrobenzene; 3-β-aminoethyloxy-4-aminonitrobenzene; 2-N-(methyl)amino-5-(N-β-amino-n-butylaminonitrobenzene; 2-N-(γ-amino-n-propyl)amino-5-N,N-(dimethyl)aminonitrobenzene; 3-methoxy-4-N-(β-aminoethyl)aminonitrobenzene; 2-N-(β-aminoethyl)amino-5-aminonitrobenzene; 2-amino-4-chloro-5-N-(β-aminoethyl)aminonitrobenzene; 2-N-(β-aminoethyl)amino-4-methoxynitrobenzene; 2-N-(β-aminoethyl)aminonitrobenzene; 2-N-(β-aminoethyl)amino-5-N-(β-aminoethyl)aminonitrobenzene; 2-N-(β-aminoethyl)amino-4-β-hydroxyethyloxynitrobenzene; 3-β-hydroxyethyloxy-4-N-(β-aminoethyl)aminonitrobenzene; 2-amino-5-aminoethyloxynitrobenzene; 3-hydroxy-4-N-(β-aminoethyl)aminonitrobenzene; 2-N-(β-aminoethyl)amino-5-β-hydroxyethyloxynitrobenzene; 2-N-(β-aminoethyl)amino-4-hydroxynitrobenzene; 2-[2-hydroxy-3-N-(β-hydroxyethyl)amino-6-nitro]benzyloxy]ethylamine and 2-[2-hydroxy-3-N-(β-hydroxypropyl)amino-6-nitro]benzyloxy]ethylamine.

Among the nitrobenzene dyes of formula (X) above, the following are most particularly preferred: 2-amino-4-methyl-5-N-(β-hydroxyethyl)aminonitrobenzene; 4-N-(β-ureidoethyl)aminonitrobenzene; 4-(N-ethyl-N-β-hydroxyethyl)amino-1-N-(β-hydroxyethyl)aminonitrobenzene; 2-N-(β-hydroxyethyl)amino-5-methylnitrobenzene; 5-chloro-3-N-(ethyl)amino-4-hydroxynitrobenzene; 5-amino-3-chloro-4-hydroxynitrobenzene; 2-N-(γ-hydroxypropyl)amino-5-N,N-bis(β-hydroxyethyl)aminonitrobenzene; 5-hydroxy-2-N-(γ-hydroxypropyl)aminonitrobenzene; 1,3-bis(β-hydroxyethyl)amino-4-chloro-6-nitrobenzene; 3,4-diaminonitrobenzene; 2-amino-5-hydroxynitrobenzene; 2-amino-3-hydroxynitrobenzene; 2-amino-5-N-(β-hydroxyethyl)aminonitrobenzene; 2-amino-5-N,N-bis(β-hydroxyethyl)aminonitrobenzene; 2-N-(β-hydroxyethyl)amino-5-N,N-bis(β-hydroxyethyl)aminonitrobenzene; 2-N-(β-hydroxyethyl)amino-5-hydroxynitrobenzene; 2-N-(β-hydroxyethyl)amino-5-aminonitrobenzene; 2-N-(β-aminoethyl)amino-4-methoxynitrobenzene; and 2-N-(β-aminoethyl)amino-5-β-hydroxyethyloxynitrobenzene.

According to a particular embodiment, the direct dye(s) are chosen from porphyrins and phthalocyanines, alone or as mixtures.

According to a particular embodiment, the direct dye(s) of the invention are cationic.

Examples of suitable direct dyes that may be mentioned include azo direct dyes; (poly)methine dyes such as cyanines, hemicyanines and styryl dyes; carbonyl dyes; azine dyes; nitro(hetero)aryl dyes; tri(hetero)arylmethane dyes; porphyrin dyes; phthalocyanine dyes, and natural direct dyes, alone or as mixtures.

Preferentially, the direct dye(s) contain at least one quaternized cationic chromophore or at least one chromophore bearing a quaternized or quaternizable cationic group.

According to a specific embodiment of the invention, the direct dyes comprise at least one quaternized cationic chromophore.

Mention may in particular be made, for the cationic azo dyes, of those resulting from the cationic dyes described in the Kirk-Othmer Encyclopedia of Chemical Technology, "Dyes, Azo", J. Wiley & Sons, updated on 19 Apr. 2010.

Mention may be made, among the azo dyes which can be used according to the invention, of the cationic azo dyes described in patent applications WO 95/15144, WO 95/01772 and EP 714 954.

According to a preferred embodiment of the invention, the direct dye(s) are chosen from cationic dyes known as "basic dyes".

Mention may be made, among the azo dyes described in the Colour Index International, 3rd edition, in particular of the following compounds: Basic Red 22, Basic Red 76, Basic Yellow 57, Basic Brown 16 and Basic Brown 17.

Among the cationic quinone dyes, those mentioned in the abovementioned Colour Index International are suitable and, among these, mention may be made, inter alia, of the following dyes: Basic Blue 22 and Basic Blue 99.

Among the azine dyes which are suitable, mention may be made of those listed in the Colour Index International, for example of the following dyes: Basic Blue 17, Basic Red 2.

Among the cationic triarylmethane dyes which may be used according to the invention, mention may be made, in addition to those listed in the Colour Index, of the following dyes: Basic Green 1, Basic Violet 3, Basic Violet 14, Basic Blue 7 and Basic Blue 26.

Mention may also be made of the cationic dyes described in the documents U.S. Pat. No. 5,888,252, EP 1 133 975, WO 03/029 359, EP 860 636, WO 95/01772, WO 95/15144 and EP 714 954. Mention may also be made of those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

Preferably, the cationic direct dyes are chosen from those resulting from dyes of azo and hydrazono type.

According to a specific embodiment, the direct dyes are cationic azo dyes, described in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. Nos. 3,524,842, 5,879,413, EP 1 062 940, EP 1 133 976, GB 738 585, DE 2 527 638, FR 2 275 462, GB 1974-27645, *Acta Histochem.* (1978), 61(1), 48-52; *Tsitologiya* (1968), 10(3), 403-5; *Zh. Obshch. Khim.* (1970), 40(1), 195-202; *Ann. Chim.* (Rome) (1975), 65(5-6), 305-14; *J. Chinese Chem. Soc.* (Taipei) (1998), 45(1), 209-211; *Rev. Roum. Chim.* (1988), 33(4), 377-83; *Text. Res. J.* (1984), 54(2), 105-7; *Chim. Ind.* (Milan) (1974), 56(9), 600-3; *Khim. Tekhnol.* (1979), 22(5), 548-53; *Ger. Monatsh. Chem.* (1975), 106(3), 643-8; *MRL Bull. Res. Dev.* (1992), 6(2), 21-7; *Lihua Jianyan, Huaxue Fence* (1993), 29(4), 233-4; *Dyes Pigm.* (1992), 19(1), 69-79; and *Dyes Pigm.* (1989), 11(3), 163-72.

Preferably, the cationic direct dye(s) comprise a quaternary ammonium group; more preferentially, the cationic charge is endocyclic.

These cationic radicals are, for example, a cationic radical:

bearing an exocyclic (di/tri)($C_1$-$C_8$)alkylammonium charge, or bearing an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic dyes of formulae (XII) and (XIII), and the azo cationic dyes of formulae (XIV) and (XV) below:

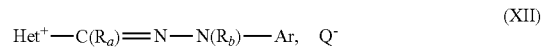  (XII)

  (XIII)

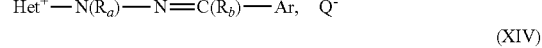  (XIV)

  (XV)

in which formulae (XII) to (XV):

$Het^+$ representing a cationic heteroaryl radical, preferentially bearing an endocyclic cationic charge, such as imidazolium, indolium or pyridinium, optionally substituted, preferentially with at least one ($C_1$-$C_8$) alkyl group such as methyl;

$Ar^+$ represents an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar″ represents an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R_a$ et $R_b$, which may be identical or different, represent a hydrogen atom or a ($C_1$-$C_8$)alkyl group, which is optionally substituted, preferentially with a hydroxyl group;

or else the $R_a$ substituent with a substituent of $Het^+$ and/or $R_b$ with a substituent of Ar form, together with the atoms that bear them, a (hetero)cycloalkyl; in particular, $R_a$ and $R_b$ represent a hydrogen atom or a ($C_1$-$C_4$) alkyl group optionally substituted with a hydroxyl group;

$Q^-$ represents an organic or mineral anionic counterion, such as a halide or an alkyl sulfate.

In particular, mention may be made of the azo and hydrazono direct dyes bearing an endocyclic cationic charge of formulae (XII) to (XV) as defined previously; more particularly the cationic direct dyes of formulae (XII) to (XV) bearing an endocyclic cationic charge, described in patent applications WO 95/15144, WO 95/01772 and EP 714 954; preferentially the following direct dyes:

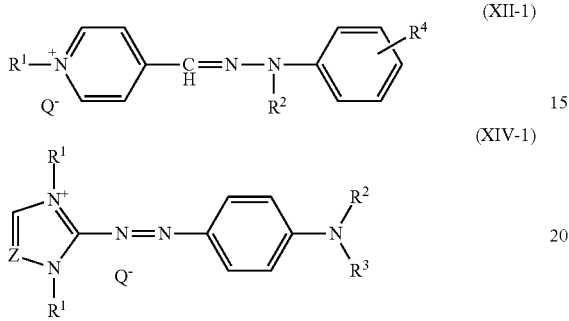

in which formulae (XII-1) and (XIV-1):

$R^1$ represents a ($C_1$-$C_4$)alkyl group such as methyl;

$R^2$ and $R^3$, which may be identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom, Z represents a CH group or a nitrogen atom, preferentially CH, Q⁻ is an anionic counterion as defined above, in particular a halide, such as chloride, or an alkyl sulfate, such as methyl sulfate or mesityl.

Particularly, the dyes of formulae (XII-1) and (XIV-1) are chosen from Basic Red 51, Basic Yellow 87 and Basic Orange 31 or derivatives thereof:

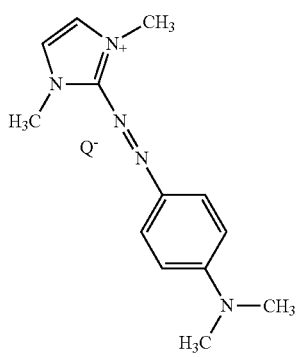

Basic Red 51

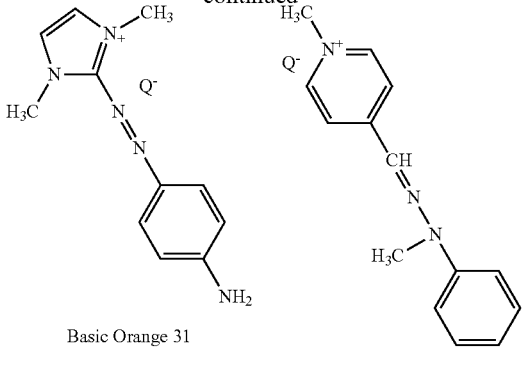

Basic Orange 31

Basic Yellow 87 with Q' being an anionic counterion as defined above, in particular a halide, such as chloride, or an alkyl sulfate, such as methyl sulfate or mesityl.

According to a specific embodiment of the invention, the direct dyes are fluorescent, i.e. they comprise at least one fluorescent chromophore as defined above.

Mention may be made, as fluorescent dyes, of the radicals resulting from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamines (such as dansyls), oxadiazoles, oxazines, perilones, perinones, perylenes, polyenes/carotenoids, squaranes, stilbenes and xanthenes.

Mention may also be made of the fluorescent dyes described in the documents EP 1 133 975, WO 03/029 359, EP 860 636, WO 95/01772, WO 95/15144 and EP 714 954 and those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons, and in the handbook—"A Guide to Fluorescent Probes and Labeling Technologies", 10th Ed., Molecular Probes/Invitrogen—Oregon 2005, circulated on the Internet or in the preceding printed editions.

According to a preferred variant of the invention, the fluorescent dye(s) are cationic and comprise at least one quaternary ammonium radical, such as those of formula (XV) below:

$$W^+—[C(R_c)=C(R_d)]_m—Ar,Q^- \qquad (XV)$$

in which formula (XV):

W⁺ represents a cationic heterocyclic or heteroaryl group, particularly comprising a quaternary ammonium optionally substituted with one or more ($C_1$-$C_8$)alkyl groups optionally substituted especially with one or more hydroxyl groups;

Ar represents an aryl group such as phenyl or naphthyl, optionally substituted preferentially with i) one or more halogen atoms such as chlorine or fluorine; ii) one or more ($C_1$-$C_8$)alkyl and preferably ($C_1$-$C_4$)alkyl groups such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino or (di)($C_1$-$C_8$)

alkylamino groups, preferably with the $C_1$-$C_4$ alkyl part optionally substituted with one or more hydroxyls, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

m' represents an integer between 1 and 4 inclusively, and in particular m has the value 1 or 2; more preferentially 1;

$R_c$ and $R_d$, which may be identical or different, represent a hydrogen atom or an optionally substituted ($C_1$-$C_8$) alkyl group, preferentially of $C_1$-$C_4$, or alternatively $R_c$ contiguous with $W^+$ and/or $R_d$ contiguous with Ar form, with the atoms that bear them, a (hetero)cycloalkyl; particularly, $R_c$ is contiguous with $W^+$ and they form a (hetero)cycloalkyl such as cyclohexyl;

$Q^-$ is an organic or mineral anionic counterion as defined previously.

According to a particular embodiment of the invention, the direct dyes are natural.

Mention may be made especially of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions containing these natural dyes and in particular henna-based poultices or extracts.

The direct dye(s) more particularly represent from 0.001% to 10% by weight and preferably from 0.005% to 6% by weight of the total weight of the composition(s) contained in the packaging article.

The packaging article may also contain at least one oxidation dye chosen from oxidation bases optionally combined with at least one coupler. More particularly, the oxidation bases are chosen from para-phenylenediamines, bis(phenyl)alkylenediamines, para-aminophenols, ortho-aminophenols and heterocyclic bases, and the addition salts thereof.

The article may also contain one or more couplers that are conventionally used for dyeing keratin fibres. Among these couplers, mention may be made especially of meta-phenylenediamines, meta-aminophenols, meta-diphenols, naphthalene-based couplers and heterocyclic couplers, and also the addition salts thereof.

In general, the addition salts of the oxidation bases and of the couplers that may be used in the context of the invention are in particular chosen from addition salts with an acid such as hydrochlorides, hydrobromides, sulfates, citrates, succinates, tartrates, lactates, tosylates, benzenesulfonates, phosphates and acetates.

According to a preferred embodiment, the direct dye(s) are mixed with the oxidation dye(s) in the same cavity.

According to another variant, the direct dye(s) are in the packaging article separated from the oxidation dye(s) by one or more laps as defined previously defining a cavity in which the said direct dye(s) are housed. According to one variant, the direct dye(s) are found mixed with the chemical oxidizing agents and separated from the oxidation dyes by a lap.

When they are present, the oxidation dye(s) more particularly represent from 0.001% to 10% by weight relative to the total weight and preferably from 0.005% to 6% by weight relative to the total weight of the composition(s) contained in the packaging article.

iii) Oxidizing Agent:

The packaging article of the invention may comprise one or more anhydrous oxidizing agents iii), preferably in powder or paste form.

More particularly, the anhydrous chemical oxidizing agent(s) iii) are chosen from peroxygenated salts, for instance persulfates, perborates, peracids and precursors thereof, percarbonates of alkali metals or alkaline-earth metals, such as sodium carbonate peroxide also known as sodium percarbonate and peracids and precursors thereof; peroxygenated salts, for instance persulfates, perborates, peracids and precursors thereof, percarbonates of alkali metals or alkaline-earth metals such as sodium carbonate peroxide also known as sodium percarbonate and peracids and precursors thereof: alkali metal bromates or ferricyanides, hydrogen peroxide-generating solid chemical oxidizing agents such as urea peroxide and polymeric complexes that can release hydrogen peroxide, especially those comprising a heterocyclic vinyl monomer such as polyvinylpyrrolidone/$H_2O_2$ complexes, in particular in the form of powders; oxidases that produce hydrogen peroxide in the presence of a suitable substrate (for example glucose in the case of glucose oxidase or uric acid with uricase).

According to a particular embodiment, the chemical oxidizing agent iii) is chosen from complexes of hydrogen peroxide and of polymer containing as monomer at least one heterocyclic vinyl monomer.

More particularly, the heterocyclic vinyl monomer is chosen from monomers comprising a 4- to 6-membered heterocycle, optionally fused to a benzene ring and optionally comprising from 1 to 4 identical or different endocyclic heteroatoms; the number of endocyclic heteroatoms being less than the number of ring members of the heterocycle. Preferably, the number of endocyclic heteroatoms is 1 or 2.

More particularly, the heteroatom(s) are chosen from sulfur, oxygen and nitrogen, preferably from nitrogen and oxygen. In accordance with an even more advantageous embodiment of the invention, the monomer comprises at least one endocyclic nitrogen atom.

The vinyl heterocycle may optionally be substituted with one or more $C_1$-$C_4$ and preferably $C_1$-$C_2$ alkyl groups.

Preferably, the heterocyclic monomer is chosen from N-vinyl monomers.

Among the monomers that may be envisaged, mention may be made of the following optionally substituted monomers: N-vinylpyrrolidone, vinylcaprolactam, N-vinylpiperidone, N-vinyl-3-morpholine, N-vinyl-4-oxazolinone, 2-vinylpyridine, 4-vinylpyridine, 2-vinylquinoline, 1-vinylimidazole and 1-vinylcarbazole. Preferably, the monomer is optionally substituted N-vinylpyrrolidine.

According to a particularly advantageous embodiment of the invention, the polymer is a homopolymer.

However, it is not excluded to use a copolymer. In such a case, the comonomer(s) are chosen from vinyl acetate, (meth)acrylic acids, (meth)acrylamides and $C_1$-$C_4$ alkyl esters of (meth)acrylic acid, which may be substituted or unsubstituted.

The polymer participating in this complex is preferably water-soluble. It may have variable average molecular weights, preferably between $10^3$ and $3 \times 10^6$ g/mol and preferably between $10^3$ and $2 \times 10^6$ g/mol. It is also possible to use mixtures of such polymers.

Advantageously, the said complex comprises from 10% to 30% by weight, more particularly from 13% to 25% by weight and preferably from 18% to 22% by weight of hydrogen peroxide relative to the total weight of the complex.

According to an even more advantageous variant of the invention, in this complex, the mole ratio between the heterocyclic vinyl monomer(s) and the hydrogen peroxide ranges from 0.5 to 2 and preferably from 0.5 to 1.

This complex is advantageously in the form of a substantially anhydrous powder.

Complexes of this type are especially described in U.S. Pat. Nos. 5,008,106, 5,077,047, EP 832 846, EP 714 919, DE 4344131 and DE 195 45 380 and the other polymer complexes described in U.S. Pat. Nos. 5,008,093, 3,376,110 and 5,183,901.

Examples of complexes that may be mentioned include products such as Peroxydone K-30, Peroxydone K-90 and Peroxydone XL-10 and also complexes formed with hydrogen peroxide and one of the following polymers such as Plasdone K-17, Plasdone K-25, Plasdone K-29/32, Plasdone K-90, Polyplasdone INF-10, Polyplasdone XL-10, Polyplasdone XL, Plasdone S-630, Styleze 2000 Terpolymer and the series of Ganex copolymers, sold by the company ISP.

According to a particular embodiment of the invention, the packaging article contains one or more solid chemical oxidizing agents chosen from a) urea peroxide, b) polymer complexes that can release hydrogen peroxide, chosen from polyvinylpyrrolidone/$H_2O_2$ complexes; c) perborates and d) percarbonates; preferably, the packaging article contains as chemical oxidizing agents one or more percarbonates.

The packaging article according to the invention advantageously contains from 0.1% to 70% by weight and preferably from 1% to 55% by weight of chemical oxidizing agent relative to the total weight of the packaging article.

According to one variant, the packaging article of the invention does not comprise any oxidizing agent.

According to this variant, if it is necessary to perform the colouring in the presence of an oxidizing agent, then the packaging article may be either first dissolved in an aqueous composition to which is then added at least one chemical oxidizing agent, or directly dissolved in an oxidizing composition comprising at least one chemical oxidizing agent. In this case, the chemical oxidizing agent may be a chemical oxidizing agent such as hydrogen peroxide.

The oxidizing agent may also be added to the aqueous composition in the form of a packaging article as defined previously, but not containing any direct dyes.

Other Ingredients

The packaging article may contain other ingredients. The packaging article may contain iv) one or more alkaline agents. The alkaline agent(s) may be in the packaging article either combined with the dyes, or separated from the dyes by one or more laps as defined previously.

The alkaline agent(s) are more particularly chosen from silicates and metasilicates such as alkali metal metasilicates, alkali metal or alkaline-earth metal carbonates or hydrogen carbonates, such as lithium, sodium, potassium, magnesium, calcium or barium, and mixtures thereof.

Preferably, the alkaline agent(s) are chosen from alkali metal silicates, metasilicates and carbonates, and mixtures thereof.

The concentration of alkaline agents advantageously represents from 0.01% to 40% by weight and preferably from 0.1% to 30% by weight relative to the total weight of the composition(s) contained in the packaging article.

According to a particular embodiment of the invention, the packaging article contains v) one or more ammonium salts. The ammonium salt(s) that may be in the packaging article are either combined with the direct dye(s), or separated from the dyes by one or more water-soluble laps as defined previously defining a cavity in which the said salt(s) are housed.

According to a particular variant, the packaging article comprises one or more ammonium salts chosen from ammonium halides such as ammonium chloride, ammonium sulfate, ammonium phosphate and ammonium nitrate.

In accordance with an even more advantageous embodiment of the invention, the ammonium salt is ammonium chloride or ammonium sulfate.

The concentration of ammonium salt(s), if they are present, is advantageously between 0.01% and 40% by weight relative to the total weight of the composition(s) contained in the packaging article, and preferably from 0.1% to 30% by weight relative to the total weight of the composition(s) contained in the packaging article.

When the dye composition is in paste form, it also comprises vi) one or more liquid fatty substances.

For the purposes of the present invention, the term "liquid" means any compound that is capable of flowing at room temperature, generally between 15° C. and 40° C., and at atmospheric pressure, under the action of its own weight.

Examples of liquid fatty substances that may be mentioned include the polydecenes of formula $C_{10n}H_{[(20n)+2]}$ in which n ranges from 3 to 9 and preferably from 3 to 7, esters and in particular esters of fatty alcohols or of fatty acids, sugar esters or diesters of $C_{12}$-$C_{24}$ fatty acids, cyclic esters, cyclic ethers, silicone oils, mineral oils, plant oils or animal oils, or mixtures thereof.

Preferably, the liquid fatty substance(s) are chosen from the polydecenes of formula $C_{10n}H_{[(20n)+2]}$ in which n ranges from 3 to 9 and preferably from 3 to 7, esters of fatty alcohols or of fatty acids, liquid petroleum jelly and liquid paraffin, and mixtures thereof.

Preferably, one or more mineral oils may be in the packaging article, in particular combined with the direct dye(s), for instance liquid paraffin or petroleum jelly, preferably petroleum jelly.

In the composition(s) contained in the packaging article, the content of liquid fatty substance(s), if they are present, advantageously ranges from 10% to 50% by weight relative to the weight of the composition(s) contained in the packaging article, and preferably from 20% to 50% by weight relative to the weight of the composition(s) contained in the packaging article.

The anhydrous composition according to the invention in paste form comprising a liquid fatty substance may be advantageously prepared by dispersing, under mechanical action, all of the compounds that are in powder form in the liquid fatty substance, in which the other liquid compounds of the composition have been predispersed or premixed.

The paste may also be prepared by extrusion, by introducing the liquid and solid phases of the composition into an extruder and then mixing them at a temperature below 25° C. using a co-rotating twin-screw system composed of transportation and blending elements.

According to a particular embodiment, the packaging article of the invention comprises vii) one or more thickening polymers, these polymers possibly being in the said article either with the direct dye(s) or separated from the other ingredients by one or more water-soluble laps as defined previously.

Advantageously, the thickening polymers are chosen from the following polymers:
(a) nonionic amphiphilic polymers comprising at least one fatty chain and at least one hydrophilic unit;
(b) anionic amphiphilic polymers comprising at least one hydrophilic unit and at least one fatty-chain unit;
(c) crosslinked acrylic acid homopolymers;
(d) crosslinked homopolymers of 2-acrylamido-2-methylpropanesulfonic acid, and crosslinked acrylamide copolymers thereof which are partially or totally neutralized;

(e) ammonium acrylate homopolymers or copolymers of ammonium acrylate and of acrylamide;
(f) dimethylaminoethyl methacrylate homopolymers quaternized with methyl chloride or dimethylaminoethyl methacrylate copolymers quaternized with methyl chloride and acrylamide;
(g) polysaccharides such as:
  (g1) scleroglucan gums (biopolysaccharide of microbial origin);
  (g2) gums derived from plant exudates, such as gum arabic, ghatti gum, karaya gum or gum tragacanth; and
  (g3) celluloses and derivatives;
  (g4) guar gums and derivatives; or
  (g5) starches or derivatives.

It should be noted that, in the case of the present invention, the thickening polymers act on the viscosity of the ready-to-use composition, i.e. the composition resulting from the mixing of the packaging article according to the invention with an aqueous composition.

According to the invention, amphiphilic polymers are more particularly hydrophilic polymers that are capable, in the medium of the composition, and more particularly an aqueous medium, of reversibly combining with each other or with other molecules.

Their chemical structure more particularly comprises at least one hydrophilic region and at least one hydrophobic region. The term "hydrophobic group" means a radical or polymer bearing a saturated or unsaturated, linear or branched hydrocarbon-based chain, comprising at least 8 carbon atoms, preferably at least 10 carbon atoms, preferably from 10 to 30 carbon atoms, in particular from 12 to 30 carbon atoms and more preferentially from 18 to 30 carbon atoms. Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

The thickening polymers are preferably used in an amount that may range from 0.01% to 15% by weight relative to the weight of the composition(s) contained in the packaging article, and preferably from 0.1% to 10% by weight relative to the weight of the composition(s) contained in the packaging article.

According to a particular embodiment, the packaging article of the invention comprises viii) one or more surfactants. These surfactants may be in the said article either with the direct dye(s), or separated from the other ingredients by one or more water-soluble laps as defined previously, which define a cavity in which the surfactant(s) are housed. Preferably, viii) is found with the direct dye(s) in the packaging article.

For the purposes of the present invention, the term "surfactant" means an agent comprising at least one hydrophilic group and at least one lipophilic group in its structure, and which is preferably capable of reducing the surface tension of water, and comprising in its structure, as optional repeating units, only alkylene oxide units and/or sugar units and/or siloxane units. Preferably, the lipophilic group is a fatty chain comprising from 8 to 30 carbon atoms.

This or these surfactants may be chosen from anionic, amphoteric, nonionic and cationic surfactants, or mixtures thereof. More particularly, the surfactants are chosen from nonionic and anionic surfactants.

The surfactants that are suitable for implementing the present invention are especially the following:

(a) Anionic Surfactant(s):

The term "anionic surfactant" means a surfactant comprising, as ionic or ionizable groups, only anionic groups. These anionic groups are preferably chosen from the groups —C(O)OH, —C(O)O—, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as those derived from an alkali metal, an alkaline-earth metal, an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, a-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

In particular, it is preferred to use ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds. Better still, it is preferred to use sodium lauryl ether sulfate, in particular those containing 2.2 mol of ethylene oxide, more preferentially ($C_{12}$-$C_{20}$) alkyl sulfates such as an alkali metal lauryl sulfate such as sodium lauryl sulfate.

(b) Amphoteric Surfactant(s):

The amphoteric or zwitterionic surfactant(s) of the invention are preferably non-silicone, and are especially derivatives of optionally quaternized aliphatic secondary or tertiary amines, in which derivatives the aliphatic group is a linear or branched chain comprising from 8 to 22 carbon atoms, the said amine derivatives containing at least one anionic group, for instance a carboxylate, sulfonate, sulfate, phosphate or phosphonate group. Mention may be made in particular of ($C_8$-$C_{20}$)alkyl betaines, sulfobetaines, ($C_8$-$C_{20}$) alkylamido($C_3$-$C_8$)alkyl betaines and ($C_8$-$C_{20}$)alkylamido ($C_6$-$C_8$)alkyl sulfobetaines.

Among the amphoteric or zwitterionic surfactants mentioned above, use is preferably made of ($C_8$-$C_{20}$)alkyl betaines such as cocoyl betaine, and ($C_8$-$C_{20}$)alkylamido ($C_3$-$C_8$)alkyl betaines such as cocamidopropyl betaine, and mixtures thereof. More preferably, the amphoteric or zwitterionic surfactant(s) are chosen from cocamidopropyl betaine and cocoyl betaine.

(c) Cationic Surfactant(s):

The cationic surfactant(s) that may be used in the composition according to the invention comprise, for example, optionally polyoxyalkylenated primary, secondary or tertiary fatty amine salts, quaternary ammonium salts, and mixtures thereof.

Among the cationic surfactants that may be present in the composition according to the invention, it is more particularly preferred to choose from cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

(d) Nonionic Surfactant(s):

Examples of nonionic surfactants that may be used in the composition used according to the invention are described, for example, in the *Handbook of Surfactants* by M. R. Porter, published by Blackie & Son (Glasgow and London), 1991, pp. 116-178.

Examples of nonionic surfactants that may be mentioned include:

oxyalkylenated ($C_8$-$C_{24}$)alkylphenols;

saturated or unsaturated, linear or branched, oxyalkylenated or glycerolated $C_8$-$C_{30}$ alcohols;

saturated or unsaturated, linear or branched, oxyalkylenated $C_8$-$C_{30}$ amides;

esters of saturated or unsaturated, linear or branched, $C_8$-$C_{30}$ acids and of polyethylene glycols;

polyoxyethylenated esters of saturated or unsaturated, linear or branched, $C_8$-$C_{30}$ acids and of sorbitol;

fatty acid esters of sucrose;

($C_8$-$C_{30}$)alkylpolyglycosides, ($C_8$-$C_{30}$)alkenylpolyglycosides, optionally oxyalkylenated (0 to 10 oxyalkylene units) and comprising 1 to 15 glucose units, ($C_8$-$C_{30}$) alkylglucoside esters;

saturated or unsaturated, oxyethylenated plant oils;

condensates of ethylene oxide and/or of propylene oxide, inter alia, alone or as mixtures;

N—($C_8$-$C_{30}$)alkylglucamine and N—($C_8$-$C_{30}$)acylmethylglucamine derivatives;

aldobionamides;

amine oxides;

oxyethylenated and/or oxypropylenated silicones;

the surfactants containing a number of moles of ethylene oxide and/or of propylene oxide ranging advantageously from 1 to 100, more particularly from 2 to 100, preferably from 2 to 50 and more advantageously from 2 to 30. Advantageously, the nonionic surfactants do not comprise any oxypropylene units.

In accordance with a preferred embodiment of the invention, the nonionic surfactants are chosen from oxyethylenated $C_8$-$C_{30}$ alcohols comprising from 1 to 100 mol and more particularly from 2 to 100 mol of ethylene oxide; polyoxyethylenated esters of saturated or unsaturated, linear or branched $C_8$-$C_{30}$ acids and of sorbitan comprising from 1 to 100 mol and better still from 2 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols preferably correspond to formula (A8) below:

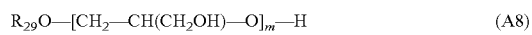

$$R_{29}O\text{---}[CH_2\text{---}CH(CH_2OH)\text{---}O]_m\text{---}H \qquad (A8)$$

in which formula (A8):

$R_{29}$ represents a linear or branched $C_8$-$C_{40}$ and preferably $C_8$-$C_{30}$ alkyl or alkenyl radical; and m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferentially, the nonionic surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated, monoglycerolated or polyglycerolated surfactants and alkylpolyglucosides.

Even more preferentially, the nonionic surfactants are chosen from polyoxyethylenated sorbitan esters, polyoxyethylenated fatty alcohols and alkylpolyglucosides, and mixtures thereof.

The surfactant(s) when they are present, more particularly represent from 0.01% and 60% by weight relative to the total weight of the composition(s) included in the packaging article, preferably between 0.5% and 30% by weight and even more preferentially between 1% and 20% by weight of the composition(s) included in the packaging article.

According to a particular embodiment, the packaging article of the invention comprises ix) one or more cationic or amphoteric substantive polymers. These polymers may be found in the said article either with the direct dye(s), or separated from the other ingredients by one or more water-soluble laps as defined previously, which define a cavity in which the substantive polymer(s) are housed. Preferably, the agents ix) are found with the direct dye(s) in the packaging article. More particularly, the substantive polymers are chosen from cationic polymers.

The substantive nature (i.e. the capacity for deposition onto the hair) of the polymers is conventionally determined using the test described by Richard J. Crawford, Journal of the Society of Cosmetic Chemists, 1980, 31-(5)-pages 273 to 278 (detection with Red 80 acid dye).

These substantive polymers are especially described in the literature in patent application EP-A-0 557 203.

Among the substantive polymers of the dimethyldiallylammonium halide homopolymer or copolymer type that may be used according to the invention, mention may be made in particular of:
- diallyldimethylammonium chloride polymers such as Polyquaternium-6;
- the copolymers of diallyldimethylammonium chloride and of acrylic acid such as that with proportions (80/20 by weight) sold under the name Merquat 280 Dry by the company Calgon;
- copolymers of dimethyldiallylammonium chloride and of acrylamide.

Among the substantive polymers of the methacryloyloxyethyltrimethylammonium halide polymer type that may be used according to the invention, mention may be made in particular of the products that are known in the CTFA dictionary (5th edition, 1993) as Polyquaternium 37, Polyquaternium 32 and Polyquaternium 35, which correspond respectively, as regards Polyquaternium 37, to crosslinked poly(methacryloyloxyethyltrimethylammonium chloride), in dispersion at 50% in mineral oil, and sold under the name Salcare SC95 by the company Allied Colloids; as regards Polyquaternium 32, to the crosslinked copolymer of acrylamide and methacryloyloxyethyltrimethylammonium chloride (20/80 by weight), in dispersion at 50% in mineral oil, and sold under the name Salcare SC92 by the company Allied Colloids; and as regards Polyquaternium 35, to the methosulfate of the methacryloyloxyethyltrimethylammonium/methacryloyloxyethyldimethylacetylammonium copolymer.

The substantive polymers of the quaternary polyammonium type that may be used according to the invention are as follows:
- polymers consisting of repeating units corresponding to formula ($\alpha$) below:
  —$(CH_3)_2N^+$—$(CH_2)_3$—$(CH_3)_2N^+$—$(CH_2)_6$—, $2X^-$ with $X^-$, which may be identical or different, representing an anionic counterion as defined previously, in particular a halide such as $Cl^-$, these polymers being prepared and described in French patent 2 270 846; preference is given to the polymers with repeating units of formula ($\alpha$) whose molecular weight, determined by gel permeation chromatography, is between 9500 and 9900;
- polymers consisting of repeating units corresponding to formula ($\beta$) below:
  —$(CH_3)_2N^+$—$(CH_2)_3$—$(CH_3)_2N^+$—$(CH_2)_3$—, $2X^-$ with $X^-$ as defined for ($\alpha$), these polymers being prepared and described in French patent 2 270 846; preference is given to the polymers with repeating units of formula ($\beta$) whose molecular weight, determined by gel permeation chromatography, is about 1200;
- polymers consisting of repeating units corresponding to formula ($\gamma$) below:
  —$(CH_3)_2N^+$—$(CH_2)_p$—N(H)—C(O)-G-N(H)—$(CH_2)_p$—$(CH_3)_2N^+$—$(CH_2)_2$—O—$(CH_2)_2$—, $2X^-$ in which p denotes an integer ranging from 1 to 6 approximately, G may represent a bond or a group —$(CH_2)_r$—C(O)— in which r denotes an integer equal to 4 or 7, these polymers being prepared and described in patents U.S. Pat. Nos. 4,157,388, 4,390,689, 4,702,906 and 4,719,282; preference is given to the polymers with repeating units of formula ($\gamma$) whose molecular weight is less than 100 000 and preferably less than or equal to 50 000.

The packaging article of the invention may also comprise other additives conventionally used in cosmetics.

The packaging article may thus comprise fillers such as clays; binders such as vinylpyrrolidone; lubricants such as polyol stearates or alkali metal or alkaline-earth metal stearates; hydrophilic or hydrophobic silicas; pigments; matt-effect agents or opacifiers such as titanium oxides; antioxidants such as erythorbic acid; reducing agents such as sodium metabisulfite; penetrants or sequestrants such as ethylenediaminetetraacetic acid or salts thereof; moisture absorbers such as amorphous silicas, certain polyacrylates that are crosslinked or modified with hydrophobic groups, for instance the products Luquasorb 1010 from BASF, Polytrap 6603 Adsorber from Amcol; buffers; dispersants; film-forming agents; preserving agents; vitamins; fragrances; ceramides; conditioning agents other than the substantive polymers ix) and the cationic surfactants mentioned above.

The composition in accordance with the invention may also comprise agents for controlling the release of oxygen, such as magnesium carbonate or magnesium oxide.

The additives and the oxygen-release control agents as defined previously may be present in an amount, for each of them, of between 0.01% and 40% by weight and preferably between 0.1% and 30% by weight relative to the total weight of the composition.

Dyeing Process

Another subject of the invention is a process for dyeing keratin fibres, especially human keratin fibres such as the hair, comprising the following steps: i) mixing the packaging article as defined previously with a composition that is capable of dissolving the envelope of the packaging article, ii) applying the resulting composition to the keratin fibres, iii) leaving the composition to stand on the fibres, iv) rinsing the said fibres, v) optionally shampooing the fibres, rinsing them and drying them.

It is clearly understood that, depending on the nature of the envelope, the composition capable of dissolving the envelope will be water or an aqueous composition when the envelope predominantly or solely contains a hydrophilic envelope, and the composition capable of dissolving the envelope will be an anhydrous organic composition or an aqueous composition comprising at least one liquid fatty substance or at least one organic solvent other than liquid fatty substances such as lower monoalcohols, for example ethanol, or such as polyols, for example propylene glycol or glycerol, when the article predominantly or solely contains lipophilic laps and envelope.

Thus, the aqueous composition may simply be water. The aqueous composition may optionally comprise at least one polar solvent. Among the polar solvents that may be used in this composition, mention may be made of organic compounds that are liquid at room temperature (25° C.) and at least partially water-miscible.

Examples that may be mentioned more particularly include alkanols such as ethyl alcohol, isopropyl alcohol, aromatic alcohols such as benzyl alcohol and phenylethyl alcohol, or polyols or polyol ethers, for instance ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

More particularly, if one or more solvents are present, their respective content in the aqueous composition ranges from 0.5% to 20% and preferably from 2% to 10% by weight relative to the weight of the said aqueous composition.

According to an advantageous variant, the packaging article comprises at least one chemical oxidizing agent iii) as defined previously. The dyeing process as defined previously then uses in the first step an aqueous composition which optionally comprises at least one basifying agent as defined previously or optionally at least one ingredient chosen from: ammonium salts v), preferably chosen from ammonium halides such as ammonium chloride, ammonium sulfate, ammonium phosphate and ammonium nitrate; organic fatty substances vi) preferably chosen from mineral oils, in particular liquid petroleum jelly; thickening polymers vii); surfactants viii), preferably nonionic or anionic surfactants, chosen in particular from ($C_{12}$-$C_{20}$)alkyl sulfates and ($C_{12}$-$C_{20}$)alkyl ether sulfates comprising from 2 to 20 ethylene oxide units, especially in the form of alkali metal salts, ammonium salts, amino alcohol salts and alkaline-earth metal salts, or a mixture of these compounds; preferably ($C_{12}$-$C_{20}$)alkyl sulfates such as an alkali metal lauryl sulfate such as sodium lauryl sulfate; and cationic or amphoteric substantive polymers ix) as defined previously.

These optional additives may be present in the packaging article.

Preferentially, the dyeing process as defined previously is such that the dilution ratio of one or more packaging articles as defined previously/the compound capable of dissolving the article(s), expressed on a weight basis, is inclusively between 10/90 and 90/10 and preferably between 10/90 and 50/50. Preferentially, this ratio is 20/80.

When the composition capable of dissolving the article is an aqueous hydrogen peroxide solution, it preferably has a pH of less than 7. The acidic pH ensures the stability of the hydrogen peroxide in the composition. It may be obtained using acidifying agents, for instance hydrochloric acid, acetic acid, etidronic acid, phosphoric acid, lactic acid or boric acid, and it may be conventionally adjusted by adding either basifying agents, for instance aqueous ammonia, monoethanolamine, diethanolamine, triethanolamine, isopropanolamine, 1,3-diaminopropane, an alkali metal or ammonium (bi)carbonate, an organic carbonate such as guanidine carbonate, or an alkali metal hydroxide, all these compounds, needless to say, possibly being taken alone or as a mixture.

The pH of the resulting mixture is usually inclusively between 7 and 12. Preferably, the pH of the said mixture is usually inclusively between 7.5 and 11.

Once the mixing has been performed to obtain the ready-to-use composition, this composition is applied to the wet or dry human keratin fibres.

The leave-on time is generally of the order of between 1 minute and 1 hour and preferably from 10 to 30 minutes. The working temperature during the process is conventionally between room temperature (between 15 and 25° C.) and 80° C. and preferably between room temperature and 60° C.

After the treatment, the human keratin fibres are optionally rinsed with water, washed with shampoo, rinsed again with water, and then dried or left to dry.

The examples that follow illustrate the invention without, however, limiting its scope.

EXAMPLES

I) The following compositions were prepared. The values are expressed as grams of active material for a composition total of 100 grams.

| Composition A (INCI US) | A1 (reference) | A2 (invention) |
|---|---|---|
| 2-Oleamido-1,3-octadecanediol | 0.01 | |
| Kaolin | | 44.17 |
| 3-Methylamino-4-nitrophenoxyethanol | 0.1 | 1.11 |
| 2-Nitro-5-glycerylmethylaniline | 0.6 | 6.67 |
| HC Violet No. 1 | 0.2 | 2.22 |
| 1-Amino-3-methyl-4(2-hydroxyethylamino)-6-nitrobenzene | | |
| HC Blue No. 2 | 1.2 | 13.33 |
| 1-β-hydroxyethylamino-2-nitro-4-bis-(β-hydroxyethyl)aminobenzene | | |
| HC Violet No. 2 | 0.6 | 6.67 |
| 3-[4-[bis-(2-hydroxyethyl)-amino]-2-nitro-phenylamino]-propan-1-ol | | |
| HC Red No. 3 | 0.03 | 0.33 |
| 1-(β-hydroxyethyl)-amino-2-nitro-4-aminobenzene | | |
| Polyaminopropyl biguanide | 0.5 | |
| Iodopropynyl butylcarbamate | 0.2 | |
| Glycol distearate | 1 | |
| *Mangifera indica* (mango) seed oil | 0.1 | |
| Fragrance | 0.4 | |
| Cellulose gum | 0.3 | |
| Xanthan gum | 0.5 | |
| Acrylates/$C_{10-30}$ alkyl acrylate crosspolymer | | 5 |
| Hydroxyethyl carboxymethyl cocamidopropylamine | 3.45 | |
| Laureth-12 | 9.35 | |
| Hydroxyethyl oleyl dimonium chloride | 1.41 | |
| Sodium lauryl sulfate | | 20 |
| pH agent | qs pH 6.7 | |
| Water | qs 100 | |
| Nonwoven of polyvinyl alcohol (PVA) fibres with a mean diameter of about 10 microns | | 0.5 |

II) Protocol for Preparing the Compositions and the Packaging Article

Composition A1 is prepared conventionally by mixing the ingredients.

The packaging article is prepared in two stages: in a first stage, the powdered ingredients are selected, including the direct dyes. The mixture of the powdered ingredients is then homogenized. In a second stage, the envelope is prepared from PVA fibres which are in the form of two nonwoven laps joined together at the periphery, but leaving a part gaping allowing the introduction of ingredients. This double lap is in the form of a disc (5 cm in diameter and 3 mm thick).

The mixture of the powdered ingredients is then introduced between the two PVA laps of the disc, and the gaping part is then hermetically closed to form a packaging article weighing 3.3 g.

III) Protocol for Evaluating the Technical Effect of the Said Compositions

The packaging article of the invention is mixed with water in a 1/9 (mass/mass) ratio in a bowl or a heating bottle.

The mixture is applied to the hair, with a leave-on time of 30 minutes.

The hair is rinsed and is then shampooed, and the hair is then dried.

The hair is dyed in the ranges of colours conventionally obtained with the direct dyeing products.

Results of the Evaluation:

| Mixture M | M1 (reference) | M2 (invention) |
|---|---|---|
| Mixture | A1 | Single-dose A2 mixed with tap water in a 1/9 ratio |
| Colour result | candied chestnut | candied chestnut |

The water-soluble packaging article does not in any way change the colouring quality of the keratin fibres when compared with the reference. In particular, in terms of intensity and chromaticity, the colouring results are very satisfactory. Furthermore, the application and localization of the compositions is easy and very pleasant, and does not go outside the areas to be treated. It should be noted that the process is very easy since it is a matter of dissolving the packaging article, which in the present case is in the form of a capsule, in water. It was also observed that the colour obtained is very uniform from the root to the end of the hairs.

IV) Comparative Data Film Vs. Fiber

The following compositions were prepared. The values are expressed as grams of active material for a composition total of 100 grams.

| Ingredients | A'1 (comparative) Amount | A'2 (invention) Amount |
|---|---|---|
| Kaolin | 57.88 | 57.88 |
| Hydroxyanthraquinone aminopropyl methyl morpholinium methosulfate | 4.96 | 4.96 |
| HC Red No. 3 | 8.62 | 8.62 |
| 1-(β-hydroxyethyl)-amino-2-nitro-4-aminobenzene | | |
| HC Yellow No. 9 | 0.57 | 0.57 |
| 1-Methoxy-3-(β-aminoethyl)amino-4-nitrobenzene, hydrochloride | | |
| Basic Red 51 | 0.72 | 0.72 |
| 2-[((4-Dimethylamino)phenyl)azo]-1,3-dimethyl-1H-imidazolium chloride | | |
| Acrylates/$C_{10}$-$C_{30}$ alkylacrylate crosspolymer | 4.85 | 4.85 |
| Polyvinyl alcohol [FILM] (Solublon PVAL-Film Type GA 40 μm) | 3 | — |
| Polyvinyl alcohol [NON WOVEN] fibres with a mean diameter of about 10 microns | — | 3 |
| Sodium lauryl sulfate | 19.4 | 19.4 |

The packaging article is prepared in two stages, in a first stage, the powdered ingredients are selected, including the direct dyes. The mixture of the powdered ingredients is then homogenized. In a second stage, the envelope is prepared from PVA which are in the form of two nonwoven laps (for invention) or film laps (for comparative) joined together at the periphery, but leaving a part gaping allowing the introduction of ingredients. This double lap is in the form of a disc (5 cm in diameter and 3 mm thick).

The mixture of the said powdered ingredients is then introduced between the two PVA laps of the disc, and the gaping part is then closed.

At the time of treatment each of composition A'1 and A'2 is mixed with water with the weight ratio of 10 parts of composition A'1 and A'2 for 90 parts of water in a bowl until total solubilisation of the ingredients and homogeneity of the mixture. Each mixture A'1+water and A'2+water is then applied on 90% natural white hair (90 NW) or permed white hair (90 PW) with a bath ratio of 10 g of mixture for 1 g of lock, with a leave-on time of 30 minutes at 27° C. The hair is rinsed and is then shampooed, and the hair is then dried.

The coloration is measured using a Minolta CM 3600 D spectrocolorimeter. The chromaticity is evaluated in the CIE L* a* b* system. In this L* a* b* system, L* represents the intensity of the colour, a* indicates the green/red colour axis and b* indicates the blue/yellow colour axis. The lower the value of L*, the darker or more intense the colour.

The value of chromaticity C* is calculated from the values of a*, b* according to equation (i) below:

$$C^* = \sqrt{a^{*2} + b^{*2}} \quad (i)$$

The greater the value of C*, the better the chromaticity of the treated fibres.

Results on Intensity L* and Chromaticity C*

| Composition | L* | a* | b* | C* |
|---|---|---|---|---|
| A1 (comparative) | 32.11 | 21.02 | −1.1 | 21.05 |
| A2 (invention) | 29.87 | 23.31 | −0.09 | 23.31 |

The chromaticity and the intensity of the mixture A2+water according to the invention with fibers are significantly higher than that obtained with the film (A1+water).

Results on Selectivity

On the other hand, for evaluating the selectivity of the colour between the root and tip of the keratin fibre, measurement can be done on permed white hair (PW) and natural white hair, wherein the variation in colouring between the coloured locks PW and the coloured natural white hair as defined by ΔE*, corresponding to the selectivity of the colour, is calculated according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_o^*$, $a_o^*$ and $b_o^*$ represent the values measured after dyeing the permed or sensitized hair. The lowest ΔE* is the best homogeneity of the hair colour.

| Composition | Hair type | L* | a* | b* | ΔE |
|---|---|---|---|---|---|
| A1 (comparative) | BN | 32.11 | 21.02 | −1.1 | 5.59 |
| | BP | 26.86 | 22.81 | −0.41 | |
| A2 (invention) | BN | 29.87 | 23.31 | −0.09 | 2.43 |
| | BP | 27.52 | 22.85 | −0.49 | |

The selectivity of the mixture A2+water according to the invention with fibers is significantly lower than that obtained with the film (A1+water) i.e. homogeneity of the color is significantly higher than the comparative one.

The invention claimed is:

1. A packaging article comprising:
   i) an envelope defining at least one cavity, the envelope-comprising water-soluble and/or liposoluble fibers;
   ii) at least one anhydrous dye composition comprising at least one direct dye chosen from anionic, nonionic, or cationic direct dyes, or mixtures thereof;
   iii) optionally at least one anhydrous oxidizing agent; and
   iv) optionally at least one thickening polymer chosen from:
      (a) nonionic amphiphilic polymers comprising at least one fatty chain and at least one hydrophilic unit;
      (b) anionic amphiphilic polymers comprising at least one hydrophilic unit and at least one fatty-chain unit;
      (c) crosslinked acrylic acid homopolymers;
      (d) crosslinked homopolymers of 2-acrylamido-2-methylpropanesulfonic acid, and crosslinked acrylamide copolymers thereof which are partially or totally neutralized;
      (e) ammonium acrylate homopolymers or copolymers of ammonium acrylate and of acrylamide; or
      (f) dimethylaminoethyl methacrylate homopolymers quaternized with methyl chloride or dimethylaminoethyl methacrylate copolymers quaternized with methyl chloride and acrylamide, wherein the anhydrous dye composition ii) and the oxidizing agent iii), when it is present, are in the at least one cavity defined by the envelope i), and wherein the packaging article is free from thickening polymers other than the at least one thickening polymer.

2. The packaging article of claim 1, wherein the anhydrous dye composition and/or the anhydrous oxidizing agent are in paste or powder form.

3. The packaging article of claim 1, wherein the envelope i) comprises at least one water-soluble polymer chosen from natural, artificial, or synthetic water-soluble polymers.

4. The packaging article of claim 1, wherein the envelope i) comprises at least one water-soluble polymer chosen from polysaccharides.

5. The packaging article of claim 1, wherein the envelope i) comprises synthetic water-soluble polymers or polyvinyl alcohol fibers.

6. The packaging article of claim 1, wherein the envelope i) is nonwoven.

7. The packaging article of claim 1, wherein the envelope i) comprises liposoluble polymer fibers.

8. The packaging article of claim 1, wherein the envelope i) comprises at least one type of fiber chosen from spun, carded or twisted fibers, wherein the at least one type of fiber has a diameter of less than about 500 μm and/or wherein the tensile strength of the at least one type of fiber is at least about 2.7 g/dtex (3 g/d).

9. The packaging article of claim 1, wherein the envelope i) comprises from about 0.5% to about 20.0% by weight relative to the total weight of the packaging article.

10. The packaging article of claim 1, wherein the at least one direct dye is chosen from: acridines; acridones; anthranthrones; anthrapyrimidines; anthraquinones; azines; (poly) azos, hydrazono or hydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines; diazines; diketopyrrolopyrroles; dioxazines; diphenylamines; diphenylmethanes; dithiazines; flavonoids; fluorindines; formazans; indamines; indanthrones; indigoids and pseudoindigoids; indophenols; indoanilines; isoindolines; isoindolinones; isoviolanthrones; lactones; (poly)methines; naphthalimides; naphthanilides; naphtholactams; naphthoquinones; nitroaromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines; thioindigos; thiopyronines; triarylmethanes, xanthenes; or mixtures thereof.

11. The packaging article of claim 1, wherein the oxidizing agent iii), is chosen from a) urea peroxide, b) polymer complexes that can release hydrogen peroxide; c) perborates; or d) percarbonates.

12. The packaging article of claim 1, further comprising at least one ingredient chosen from alkaline agents v); ammonium salts vi); liquid fatty substances vii); surfactants viii); or cationic or amphoteric substantive polymers ix).

13. The packaging article of claim 1:
wherein the envelope i) comprises a first water-soluble or liposoluble layer and a second water-soluble or liposoluble layer joined together at a peripheral region;

wherein the first layer comprises a free central region configured to face a free central region of the second layer;

wherein the free central region of the first layer and the free central region of the second layer define the cavity;

wherein the cavity comprises the dye composition comprising at least one direct dye; and wherein at least a portion of the peripheral region is closed.

14. The packaging article of claim 13, further comprising at least one third water-soluble or liposoluble layer,
wherein the third layer at least partially defines at least one additional cavity, wherein least one other ingredient is present in the at least one additional cavity and separated from the anhydrous dye composition.

15. The packaging article of claim 13, wherein the first layer and the second layer each have a thickness smaller than their other dimensions.

16. The packaging article of claim 13:
wherein the first layer is a nonwoven and the second layer is a nonwoven; and wherein at least one portion of the peripheral region of the first layer is substantially identical in shape to at least one portion of the peripheral region of the second layer.

17. A process for dyeing keratin fibers, the process comprising:
mixing a packaging article with a composition that is capable of dissolving the packaging article to form a resulting composition, the packaging article comprising:
  i) an envelope defining at least one cavity, the envelope comprising water-soluble and/or liposoluble fibers;
  ii) at least one anhydrous dye composition comprising at least one direct dye;
  iii) optionally at least one anhydrous oxidizing agent; and
  iv) optionally at least one thickening polymer chosen from:
    (a) nonionic amphiphilic polymers comprising at least one fatty chain and at least one hydrophilic unit;
    (b) anionic amphiphilic polymers comprising at least one hydrophilic unit and at least one fatty-chain unit;
    (c) crosslinked acrylic acid homopolymers;
    (d) crosslinked homopolymers of 2-acrylamido-2-methylpropanesulfonic acid, and crosslinked acrylamide copolymers thereof which are partially or totally neutralized;
    (e) ammonium acrylate homopolymers or copolymers of ammonium acrylate and of acrylamide; or
    (f) dimethylaminoethyl methacrylate homopolymers quaternized with methyl chloride or dimethylaminoethyl methacrylate copolymers quaternized with methyl chloride and acrylamide,
  wherein the anhydrous dye composition ii) and the oxidizing agent iii), when it is present, are in the at least one cavity defined by the envelope i), and
  wherein the packaging article is free from thickening polymers other than the at least one thickening polymer;
applying the resulting composition to the keratin fibers;
leaving the resulting composition on the keratin fibers;
rinsing the keratin fibers; and
optionally shampooing, rinsing, and/or drying the keratin fibers.

18. The process of claim 17, wherein the composition that is capable of dissolving the packaging article is an aqueous composition, or an organic composition comprising at least one liquid fatty substance.

19. The process of claim 17, wherein the weight ratio of the packaging article to the composition that is capable of dissolving the packaging article ranges from about 10/90 to about 50/50.

* * * * *